US006485648B1

(12) United States Patent
Gjerde et al.

(10) Patent No.: US 6,485,648 B1
(45) Date of Patent: Nov. 26, 2002

(54) MIPC COLUMN CLEANING SYSTEM AND PROCESS

(75) Inventors: Douglas T. Gjerde, Saratoga, CA (US); Robert M. Haefele, Campbell, CA (US); Laura Bunnel, Omaha, NE (US); Paul D. Taylor, Gilroy, CA (US); Kimberly A. Lamb, Omaha, NE (US); Satyajit Kar, Omaha, NE (US)

(73) Assignee: Transgenomic, Inc., San Jose, CA (US)

( * ) Notice: Subject to any disclaimer, the term of this patent is extended or adjusted under 35 U.S.C. 154(b) by 0 days.

(21) Appl. No.: 09/696,610

(22) Filed: Oct. 25, 2000

Related U.S. Application Data

(63) Continuation-in-part of application No. 09/548,983, filed on Apr. 14, 2000, which is a continuation-in-part of application No. 09/285,331, filed on Apr. 2, 1999, now Pat. No. 6,136,195, and a continuation-in-part of application No. 09/183,123, filed on Oct. 30, 1998, now Pat. No. 6,066,258, and a continuation-in-part of application No. 09/183,450, filed on Oct. 30, 1998, now Pat. No. 6,056,877, and a continuation-in-part of application No. 09/081,040, filed on May 18, 1998, now Pat. No. 5,997,742.
(60) Provisional application No. 60/161,563, filed on Oct. 26, 1999.

(51) Int. Cl.$^7$ ............................................... B01D 15/08
(52) U.S. Cl. ....................... 210/635; 210/656; 210/659; 210/198.2
(58) Field of Search ................. 210/635, 656, 210/659, 198.2; 435/6; 536/23.1, 25.4

(56) References Cited

U.S. PATENT DOCUMENTS

| 4,563,510 A | 1/1986 | Ugelstad | 526/66 |
|---|---|---|---|
| 4,683,202 A | 7/1987 | Mullis | 435/91 |
| 4,808,233 A | 2/1989 | Pfannkoch | 210/198.2 |
| 4,906,378 A | 3/1990 | Hagen et al. | 210/635 |

(List continued on next page.)

FOREIGN PATENT DOCUMENTS

| EP | 0 507 591 A2 | 10/1992 | 210/198.2 |
|---|---|---|---|
| WO | 94/11305 | 5/1994 | 210/198.2 |
| WO | 98/40395 | 9/1998 | 210/198.2 |

OTHER PUBLICATIONS

Abstract of Taylor, et al., Strand Specificy of Nicking of DNA and CHI Sites By RECBCD Enzyme, JBC online, vol. 270, No. 41: 24459–24467 (Oct. 1995).
All–Chrom Newsletter Metal Components, A Potential Source of Interference in HPLC Analysis, Alltech–Applied Science, 25:1–6 (1986).
Apffel et al. Applications of HPLC For the Analysis of Double Stranded DNA Use Of Wide Pore Silica Based Materials, ISPPP '97 17th International Symposium on the Separation of Proteins, Peptides & Polynucleotides, 26–29, (1997) pp. 1–5.
Barder et al. Fast Chromatography and Nonporous Silica, LC–GC, 15: 918–926, (1997) No. 10.

(List continued on next page.)

Primary Examiner—Ernest G. Therkorn

(57) ABSTRACT

An apparatus for effecting base pair length separations of DNA fragments by matched ion paired chromatography comprising a separation column containing separation media having non-polar DNA separation surfaces, separation solution supply means, and a separation solution conduit communicating with the separation column and the separation solution supply means, and a cleaning solution valve means positioned in the separation solution conduit for injecting cleaning solution into the separation solution conduit. A process for cleaning the non-polar DNA separation surfaces in the apparatus comprising interrupting the flow of separation solvent with a block of cleaning solution injected into the flow of separation solution passing to the column, the cleaning solution containing agent which removes accumulated residues from the non-polar surface. The cleaning solution can have an alkaline pH and contain a chelating agent such as EDTA.

15 Claims, 12 Drawing Sheets

U.S. PATENT DOCUMENTS

| | | | |
|---|---|---|---|
| 5,011,608 A | 4/1991 | Damjanovic | 210/656 |
| 5,098,539 A | 3/1992 | Shieh | 204/182.8 |
| 5,100,547 A | 3/1992 | Hardiman et al. | 210/198.2 |
| 5,112,492 A | 5/1992 | Ransohoff | 210/656 |
| 5,205,929 A | 4/1993 | Carr et al. | 210/198.2 |
| 5,207,914 A | 5/1993 | Lin | 210/635 |
| 5,242,586 A | 9/1993 | Ransohoff | 210/198.2 |
| 5,316,680 A | 5/1994 | Frechet et al. | 210/635 |
| 5,334,310 A | 8/1994 | Frechet et al. | 210/198.2 |
| 5,338,448 A | 8/1994 | Gjerde | 210/198.2 |
| 5,453,185 A | 9/1995 | Frechet et al. | 210/198.2 |
| 5,456,185 A | 10/1995 | Rother et al. | 210/198.2 |
| 5,459,039 A | 10/1995 | Modrich et al. | 435/6 |
| 5,522,994 A | 6/1996 | Frechet et al. | 210/635 |
| 5,585,236 A | 12/1996 | Bonn et al. | 435/5 |
| 5,616,701 A | 4/1997 | Woodard et al. | 536/25.4 |
| 5,651,931 A | 7/1997 | Bailey et al. | 264/126 |
| 5,698,400 A | 12/1997 | Cotton et al. | 436/6 |
| 5,738,783 A | 4/1998 | Shirota | 210/198.2 |
| 5,772,889 A | 6/1998 | Gjerde et al. | 210/635 |
| 5,795,976 A | 8/1998 | Oefner et al. | 536/25.4 |
| 5,997,742 A * | 12/1999 | Gjerde | 210/635 |
| 6,056,877 A | 5/2000 | Gjerde et al. | 210/635 |
| 6,063,283 A | 5/2000 | Shirota | 210/656 |
| 6,066,258 A | 5/2000 | Gjerde et al. | 210/635 |
| 6,129,840 A | 10/2000 | Kitaoka | 210/198.2 |
| 6,136,195 A | 10/2000 | Taylor et al. | 210/635 |

OTHER PUBLICATIONS

Berti, Dissertation, Untersuchungen Zur Ionenpaar–Umkehrphasen–Chromatographie Von DNA, Jun. 1996, pp. 52–53.

Bischoff et al, Isolation of Specific TRNAS Using an Ionic–Hydrophobic Mixed–Mode Chromatographic Matrix, Analytical Biochemistry, 151: 526–533 (1985).

Cabrera et al. Silica Rod—A New Challenge in Fast High–Performance Liquid Chromatography Separations, Trends in Analytical Chemistry, 17:50–53, (1998).

Chen et al. High–Speed High–Performance Liquid Chromatography of Peptides and Proteins, J. of Chromatography A, 705: 3–20, (1995).

Colon et al. Capillary Electrochromatography, Anal. Chem. News & Features (Aug. 1, 1997) 461A–467A.

Dadoo et al, Advances Toward the Routing Use of Capillary Electrochromatography, LC–GC, vol. 15 No. 7 (Jul. 1997) pp. 630–635.

DHPLC Workshop, Stanford University, CA, pp. 32–43 (Mar. 17, 1997).

Doris et al., Quantitative Analysis of Gene Expression By Ion–Pair High–Performance Liquid Chromatography, Journal of Chromatography, 806: 47–60, (1998).

Englehardt et al. Polymer Encapsulated Stationary Phases: Advantages, Properties and Selectivities, Chromatographia, 27: 535–543, (1989) No. 11/12.

Erikkson et al, Separation of DNA Restriction Fragments by Ion–Pair Chromatography, Journal of Chromatography, 359: 265–274 (1986).

Gelfi, et al., Detection of Point Mutations by Capillary Electorphoresis in Liquid Polymers in Temporal Thermal Gradients, Electrophoresis, 15:1506–1511 (1994).

Goodwin et al., Studies on the Preparation and Characterisation of Monodisperse Polystyrene Latices, Colloid & Polymer Sci. 252: 464–471, (1974).

Green et al. HPLC Purification of Synthetic Oligodeoxyribonucleotides Contatining Base– and Backbone–Modified Sequences, Bio Techniques 19:836–841 (1993).

Green et al. Preparative Purification of Sypercoiled Plasmid DNA for Therapeutic Applications, BioPharm, 10:52–62, (1997).

Hayward–Lester et al, Rapid Quantification of Gene Expression By Competitive RT–PCR and Ion–Pair Reversed–Phase HPLC, Bio Techniques, 20: 250–257 (1996).

Hayward–Lester et al., Quantification of Specific Nucleic Acids, Regulated RNA Processing and Genomic Polymorphisms Using Reversed–Phase HPLC. pp. 1–31 (Undated).

He et al. Fabrication of Nanocolumns for Liquid Chromatography, Anal. Chem. 70:3790–3797, (1998).

Heftman, Chromatography, 5th Edition, Journal of Chromatography Library—51A:A299–A300, (1992).

Herold et al. Recovery of Biologically Active Enzymes After HPLC Separation, BioChromatography, BioTechniques, 10:656–662, (1991).

Hewlett–Packard, ZORBAX Stable Bond ZORBAX Eclipse Reverse Phase HPLC Columns, Product Specification. pp. 1–10 Undated.

Hirabayashi et al. Size–Dependent Chromatographic Separation of Double–Stranded DNA Which is Not Based on Gel Permeation Mode, Analytical Biochemistry, 178, 336–341, (1989).

Hirabayashi, Slalom Chromatography: Size–Dependent Separation of DNA Molecules by a Hydrodynamic Phenomenon, Biochemistry, 29: 9515–9521, (1990).

http://www.transgenomic.com/html/tmha.html (May 12, 1998) pp. 1–6.

Huang et al. Large–Scale Purification of Synthetic Oligonucleotides and Carcinogen–Modified Oligodeoxynucleotides on a Reverse–Phase Polystyrene (PRP–1) Column, Analytical Biochemistry, 190:21–25, (1990).

Huber et al, High–Resolution Liquid Chromatography of Oligonucleotides on Nonporous Alkylated Styrene–Divinylbenzene Copolymers, Analytical Biochemistry, 212: 315–358 (1993).

Huber et al, High–Resolution Liquid Chromatography of DNA Fragments on Non–Porous Poly9tyrene–Divinylbenzene) Particles, Nucleic Acids Research, 21:1061–1066 (1993).

Huber et al, Rapid Analysis of Biopolymers on Modified Non–Porous Polystyrene–Divinylbenzene Particles, Chromatographia, 37: 653–658 (1993).

Huber et al, Rapid and Accurate Sizing of DNA Fragments by Ion–Pair Chromatography on Alkylated Nonporous Poly-(Styrene–Divinylbenzene) Particles, Analytical Chemistry, 67: 578–585 (1995).

Huber et al., Micropellicular Stationary Phases for High–Performance Liquid Chromatography of Double–Stranded DNA, J. of Chromatography A, 806:3–30 (1998).

Huber et al, Detection of Partial Denaturation in At–Rich DNA Fragments by Ion–Pair Reversed–Phase Chromatography, Analytical Chemistry, 68:2959–2965 (1996).

Iler et al., The Chemistry of Silica (1979) John Wiley & Sons, New York 566–569.

Issaq et al. Enthalpy and Entropy Effects for Homologous Solutes in HPLC with Alkyl Chain Bonded Phases, J. of Liquid Chromatography 12: 2067–2082, (1989).

Jinno et al. Planarity Recognition of Large Polycyclic Aromatic Hydrocarbons by Various Octadecylsilica Stationary Phases in Non–Aqueous RPLC, Chromatographia, 27:285–291, (1989).

Jorgenson et al, High–Respolution Separation Based on Electrophoresis and Electroosmosis, J. of Chromatography, 218 (1981) 209–216.

Kato et al. Separation of DNA Restriction Fragments by High–Preformance Ion–Exchange Chromatography on a Non–Porous Ion Exchanger, Journal of Chromatography, 478:264–268, (1989).

Kwiatkowski et al. Use of RP Ion Pair Chromatography to Fractionate and Purify DNA Fragments and Monomeric Components of RNA, Acta Chemica scandinavica B. 38: 721–733, (1984).

Li et al, Strategies for Faster Gradient Chromatography, LC–GC, vol. 16 No. 5 (May 1998) pp. 469–475.

Liu et al, Denaturing High Performance Liquid Chromatography (DHPLC) Used in The Detection of Germline and Somatic Mutations, Nucleic Acid Research, 26:1396–1400 (1998).

Maa et al, Rapid High–Performance Liquid Chromatography of Ncleic Acids with Polystyrene–Based Micropellicular Anion Exchangers, Journal of Chromatography, 508:61–73, (1990).

Melander et al., Mobile Phase Effects in Reversed–Phase Chromatography, J. of Chromatography 185: 99–109, (1979).

Mhatre et al., Interfacing Gradient Elution Ion–Exchange Chromatography (IEC) and Low Angle Laser Light Scattering Photometry (LALLS) for Analysis of Proteins, J. Chromatography, (1991) Jul Submitted for Publication 1–13.

Moriyama et al. New RP HPLC Column for Oligonucleotide Separtion, Journal of Chromatography, 445:225–233, (1988).

Nahum et al. Surface Silnols in Silica–Bonded Hydrocarbonaceous Stationary Phases, J. of Chromatography, 203: 53–63, (1981).

Nakanishi et al. Double Pore Silica Gel Monolith Applied to Liquid Chromatography, J. Sol–Gel Science & Technology, 8:547–552, (1997).

Nakanishi et al., Phase Separation in Silica Sol–Gel System Containing Poly(Ethylene Oxide), Bull. Chem. Soc. Jpn. 67:1327–1335, (1994).

Oefner et al, High–Performance Liquid Chromatography for Routing Analysis of Hepatitis C Virus CDNA/PCR Products, Research Reports, 16: 898–9, 902–8 (1994).

Oefner et al, High–Resolution Liquid Chromatography of Fluorescent Dye–Labeled Nucleic Acids, Analytical Biochemistry, 223: 1–8 (1994).

Oefner et al, High–Resolution Liquid Chromatography of Nucleic Acids, American Laboratory, 26:28C–28J (1994).

Oefner et al. Poster Symposium—Session 29 Comparative DNA Sequencing by Denaturing High–Performance Liquid Chromatography (DHLPC), Am. J. Human Genet., 57:A66, (1995).

Ohmiya et al., Separation of DNA Fragments by High–Resolution Ion–Exchange Chromatography on a Nonporous QA Column, Analytical Biochemistry, 189:126–130 (1990).

Petro et al, Molded Monolithic Rod of Macroprous Poly-(Styrene–Co–Divinylbenzene) as a Separation Medium for HPLC of Synthetic Polymers, Analytical Chemistry, 68: 315–321 (1996).

Poole et al. Chromatography Today Elsevier, New York, 313–342, (1991).

Pretorius et al., A New Concept for High–Speed Liquid Chromatography, J. of Chromatography, 99:23–30, (1974).

Puresyn, Inc. Communique Physical Characteristics of the Polyflo Resin, pp. 1–9, Undated.

Saiki et al., Enzymatic Amplification of B–Globin Genomic Sequences and Restriction Site Analysis for Diagnosis of Sickle Cell Anemia, Science, 230: 1350–1354, (1985).

Schoburg et al. Immobilization of Stationary Liquids in Reversed– and Normal–Phase Liquid Chromatography, J. of Chromatography, 282:27–39, 188 (1983).

Schoburg et al. Immobilization of Stationary Liquids of Silica Particles by Y–Radiation, Chromatographia, 18: 265–274, (1984).

Snyder et al, Introduction to Modern Liquid Chromatography, Chapter 13, pp. 541–574, John Wiley & Sons, Inc. New York (1979).

Snyder et al, Introduction to Modern Liquid Chromatography, 2nd Ed., pp. 204–205, 624, 630–632, John Wiley & Sons, Inc. New York (1979).

Snyder, Introduction to Modern Liquid Chromatography, pp. 110–117, John Wiley & Sons, Inc. New York (1979).

Snyder, et al., Introduction to Modern Liquid Chromatography, pp. 173–174, 274–275, John Wiley & Sons, Inc. New York (1979).

Stober et al. Controlled Growth of Monodisperse Silica Spheres in the Micron Size Range, J. of Coll. and Interface Science 26: 62–69, (1968).

Transgenomic, Inc. Technical Note General Description: DNASep. pp. 1–8 Undated.

Ugelstad et al, Swelling of Oligomer–Polymer Particles. New Methods of Preparation of Emulsions and Polymer Dispersions, Advances in Colloid and Interface Science, 13:101–140, (1980).

Wang et al, Reversed–Phase Chromatography of Small Molecules and Peptides on A Continous Rod of Macrophorous Poly(Styrene–CodivinylBenzene), Journal of Chromatography, No. 669:230–235 (1994).

Wells, et al. RPC–5 Column Chromatography for the Isolation of DNA Fragments, Methods of Enzymology, vol. 65, Nucleic Acids, Part 1, pp. 327–347, 1980.

Wheals, Chemically Bonded Phases for Liquid Chromatography, J. of Chromatography (1975) 107: 402–407.

Yau et al., Modern Size–Exclusion Liquid Chromatography, John Wiley & Sons, 1979, New York pp. 343–381.

Agilent Technologies www.chem.aglient.com/cpowcs/A25637.pdf 1–3 (downloaded Oct., 2000).

Agilent Technologies www.chem.agilent.com/cpfocs/A25883.pdf pp. 1–3–1–5 (downloaded Oct., 2000)

Collins, K. E. et al. LC–GC 18:688–692 (2000).

Collins, K. E. LC–GC 18:600–609 (2000).

Copper, et al. Human Genetics 69:201 (1985), pp. 201–203.

Cotton, TIG 13:43 (1997), pp. 43–46.

Duda, C. Current Separations 12:30–33 (1993).

Figeys, D. et al., Analytical Chemistry 330A–335A (May 1, 2000).

Guyer, et al. Proc. Natl. Acad. Sci. USA 92:10841 (1995).

Hyaward–Lester, et al. Genome Research 5:494 (1995).

Underhill, et al. Genome Res. 7:996 (1997).

Underhill, et al. Proc. Natl. Acad. Sci. USA 93:193 (1996).

717 System Cleaning and Passivation, Waters Corp. (dated Oct. 9, 2000), pp. 1 & 2.

Sofer et al, Process Chromatography, A Guide To Validation, Academic Press, 5–20 (1991).

Collins, Kenneth, et al., LCGC—Jun. 2000—LC Troubleshooting—Stainless Steel Surfaces in LC Systems, Part I—Corrosion and Erosion, pp. 1–7, 18:600–609.

* cited by examiner

MIPC COLUMN CLEANING SYSTEM AND PROCESS

RELATIONSHIP TO CO-PENDING APPLICATIONS

This application is a continuation-in-part of copending, commonly assigned patent application Ser. No. 09/548,983 filed Apr. 14, 2000, which is a continuation-in-part of application No. 09/285,331, filed Apr. 2, 1999, now U.S. Pat. No. 6,136,195, application No. 09/183,123, filed Oct. 30, 1998, now U.S. Pat. No. 6,066,258, and application No. 09/183,450, filed Oct. 30, 1998, now U.S. Pat. No. 6,056, 877 U.S. Pat. No. 6,136,195 is a continuation-in-part of U.S. application No. 09/081,040, filed May 18, 1998, now U.S. Pat. Nos. 5,997,742; 6,066,258; and 6,056,877. This application claims priority based on commonly assigned Provisional Patent Application Ser. No. 60/161,563 filed Oct. 26, 1999.

FIELD OF THE INVENTION

This invention relates to DNA separation systems suitable for effecting a size-based (base pair length) separation of DNA. In particular this invention relates to a process for restoring matched ion polynucleotide chromatography (MIPC) columns without removing them from the separation system. This process can be used to remove DNA residues from the column between separations or to regenerate columns which have become less effective as a result of extended use.

BACKGROUND OF THE INVENTION

DNA molecules are polymers comprising sub-units called deoxynucleotides. The four deoxynucleotides found in DNA comprise a common cyclic sugar, deoxyribose, which is covalently bonded to any of the four bases, adenine (a purine), guanine (a purine), cytosine (a pyrimidine), and thymine (a pyrimidine), referred to herein as A, G, C, and T respectively. A phosphate group links a 3'-hydroxyl of one deoxynucleotide with the 5'-hydroxyl of another deoxynucleotide to form a polymeric chain. In double stranded DNA, two strands are held together in a helical structure by hydrogen bonds between what are called complimentary bases. The complimentarity of bases is determined by their chemical structures. In double stranded DNA, each A pairs with a T and each G pairs with a C, i.e., a purine pairs with a pyrimidine. Ideally, DNA is replicated in exact copies by DNA polymerases during cell division in the human body or in other living organisms. DNA strands can also be replicated in vitro by means of the Polymerase Chain Reaction (PCR).

Sometimes, exact replication fails and an incorrect base pairing occurs. Further replication of the new strand produces double stranded DNA offspring containing a heritable difference in the base sequence from that of the parent. Such heritable changes in base pair sequence are called mutations.

As used herein, double stranded DNA is referred to as a duplex. When a base sequence of one strand is entirely complimentary to a base sequence of the other strand, the duplex is called a homoduplex. When a duplex contains at least one base pair which is not complimentary, the duplex is called a heteroduplex. A heteroduplex is formed during DNA replication when an error is made by a DNA polymerase enzyme and a non-complimentary base is added to a polynucleotide chain being replicated. Further replications of a heteroduplex will, ideally, produce homoduplexes which are heterozygous, i.e., these homoduplexes will have an altered sequence compared to the original parent DNA strand. When the parent DNA has a sequence which predominates in a naturally occurring population, the sequence is generally referred to as a "Wild type".

Many different types of DNA mutations are known. Examples of DNA mutations include, but are not limited to, "point mutation" or "single base pair mutations" in which an incorrect base pairing occurs. The most common point mutations comprise "transitions" in which one purine or pyrimidine base is replaced for another and "transversions" wherein a purine is substituted for a pyrimidine (and visa versa). Point mutations also comprise mutations in which a base is added or deleted from a DNA chain. Such "insertions" or "deletions" are also known as "frameshift mutations". Although they occur with less frequency than point mutations, larger mutations affecting multiple base pairs can also occur and may be important. A more detailed discussion of mutations can be found in U.S. Pat. No. 5,459,039 to Modrich (1995), and U.S. Pat. No. 5,698,400 to Cotton (1997). These references and the references contained therein are hereby incorporated by reference in their entireties.

The sequence of base pairs in DNA is a code for the production of proteins. In particular, a DNA sequence in the exon portion of a DNA chain codes for a corresponding amino acid sequence in a protein. Therefore, a mutation in a DNA sequence may result in an alteration in the amino acid sequence of a protein. Such an alteration in the amino acid sequence may be completely benign or may inactivate a protein or alter its function to be life threatening or fatal. On the other hand, mutations in an intron portion of a DNA chain would not be expected to have a biological effect since an intron section does not contain code for protein production. Nevertheless, mutation detection in an intron section may be important, for example, in a forensic investigation.

Detection of mutations is therefore of great importance in diagnosing diseases, understanding the origins of disease, and the development of potential treatments. Detection of mutations and identification of similarities or differences in DNA samples is also of critical importance in increasing the world food supply by developing diseases resistant and/or higher yielding crop strains, in forensic science, in the study of evolution and populations, and in scientific research in general (Guyer, et al., *Proc. Natl. Acad. Sci. USA* 92:10841 (1995); Cotton, *TIG* 13:43 (1997)).

Alterations in a DNA sequence which are benign or have no negative consequences are sometimes called "polymorphisms". For the purposes of this application, all alterations in the DNA sequence, whether they have negative consequences or not, are defined herein as "mutations". For the sake of simplicity, the term "mutation" is used herein to mean an alteration in the base sequence of a DNA strand compared to a reference strand (generally, a wild type). As used herein, the term "mutation" includes the term "polymorphism" or any other similar or equivalent term of art.

Prior to this invention, size based analysis of DNA samples was accomplished by standard gel electrophoresis (GEP). Capillary gel electrophoresis (CGE) has also been used to separate and analyze mixtures of DNA fragments having different lengths, e.g., the digests produced by restriction enzyme cleavage of DNA samples. However, these methods cannot distinguish DNA fragments which have the same base pair length but have a differing base sequence. This is a serious limitation of GEP.

Mutations in heteroduplex DNA strands under "partially denaturing" conditions can be detected by gel based analytical methods such as denaturing gradient gel electrophoresis (DGGE) and denaturing gradient gel capillary electrophoresis (DGGC). The term "partially denaturing" is defined to be the separation of a mismatched base pair (caused by temperature, pH, solvent, or other factors) in a DNA double strand while other portions of the double strand remain intact, that is, are not separated. The phenomenon of "partial denaturation" occurs because a heteroduplex will denature at the site of base pair mismatch at a lower temperature than is required to denature the remainder of the strand.

These gel-based techniques are difficult and require highly skilled laboratory scientists. In addition, each analysis requires a lengthy setup and separation. A denaturing capillary gel electrophoresis analysis can only be made of relatively small fragments. A separation of a 90 base pair fragment takes more than 30 minutes. A gradient denaturing gel runs overnight and requires about a day of set up time. Additional deficiencies of gradient gels are the difficulty of adapting these procedures to isolate separated DNA fragments (which requires specialized techniques and equipment), and establishing the conditions required for the isolation. The conditions must be experimentally developed for each fragment (Laboratory Methods for the Detection of Mutations and Polymorphisms, ed. G. R. Taylor, CRC Press, 1997). The long analysis time of the gel methodology is further exacerbated by the fact that the movement of DNA fragments in a gel is inversely proportional, in a geometric relationship, to the length of the DNA fragments. Therefore, the analysis time of longer DNA fragments can often be untenable.

In addition to the deficiencies of denaturing gel methods mentioned above, these techniques are not always reproducible or accurate since the preparation of a gel and running an analysis can be highly variable from one operator to another.

Separation of double stranded nucleic acid fragment mixtures by GEP or DGGE produces a linear array of bands, each band in the array representing a separated double stranded nucleic acid component of that mixture. Since many mixtures are typically separated and analyzed simultaneously in separate lanes on the same gel slab, a parallel series of such linear arrays of bands is produced. Bands are often curved rather than straight, their mobility and shape can change across the width of the gel, and lanes and bands can mix with each other. The sources of such inaccuracies stem from the lack of uniformity and homogeneity of the gel bed, electroendosmosis, thermal gradient and diffusion effects, as well as host of other factors. Inaccuracies of this sort are well known in the GEP art and can lead to serious distortions and inaccuracies in the display of the separation results. In addition, the band display data obtained from GEP separations is not quantitative or accurate because of the uncertainties related to the shape and integrity of the bands. True quantitation of linear band array displays produced by GEP separations cannot be achieved, even when the linear band arrays are scanned with a detector and the resulting data is integrated, because the linear band arrays are scanned only across the center of the bands. Since the detector only sees a small portion of any given band and the bands are not uniform, the results produced by the scanning method are not accurate and can even be misleading.

Methods for visualizing GEP and DGGE separations, such as staining or autoradiography are also cumbersome and time consuming. In addition, separation data is in hard copy form and cannot be electronically stored for easy retrieval and comparison, nor can it be enhanced to improve the visualization of close separations.

Separation of double-stranded deoxyribonucleic acids (dsDNA) fragments and detection of DNA mutations is of great importance in medicine, in the physical and social sciences, and in forensic investigations. The Human Genome Project is providing an enormous amount of genetic information and yielding new information for evaluating the links between mutations and human disorders (Guyer, et al., *Proc. NatL. Acad. Sci. USA* 92:10841 (1995)). For example, the ultimate source of disease is described by genetic code that differs from the wild type (Cotton, *TIG* 13:43 (1997)). Understanding the genetic basis of disease can be the starting point for a cure. Similarly, determination of differences in genetic code can provide powerful and perhaps definitive insights into the study of evolution and populations (Cooper, et. al., *Human Genetics vol.* 69:201 (1985)). Understanding these and other issues related to genetic coding requires the ability to identify anomalies, i.e., mutations, in a DNA fragment relative to the wild type.

Traditional chromatography is a separation process based on partitioning of mixture components between a "stationary phase" and a "mobile phase". The stationary phase is provided by the surface of solid materials Which can comprise many different materials in the form of particles or passageway surfaces of cellulose, silica gel, coated silica gel, polymer beads, polysaccharides, and the like. These materials can be supported on solid surfaces such as on glass plates or packed in a column. The mobile phase can be a liquid or a gas in gas chromatography. This invention relates to liquid mobile phases.

The separation principles are generally the same regardless of the materials used, the form of the materials, or the apparatus used. The different components of a mixture have different respective degrees of solubility in the stationary phase and in the mobile phase. Therefore, as the mobile phase flows over the stationary phase, there is an equilibrium in which the sample components are partitioned between the stationary phase and the mobile phase. As the mobile phase passes through the column, the equilibrium is constantly shifted in favor of the mobile phase. This occurs because the equilibrium mixture, at any time, sees fresh mobile phase and partitions into the fresh mobile phase. As the mobile phase is carried down the column, the mobile phase sees fresh stationary phase and partitions into the stationary phase. Eventually, at the end of the column, there is no more stationary phase and the sample simply leaves the column in the mobile phase.

A separation of mixture components occurs because the mixture components have slightly different affinities for the stationary phase and/or solubilities in the mobile phase, and therefore have different partition equilibrium values. Therefore, the mixture components pass down the column at different rates.

Since chromatographic separations depend on interactions with the stationary phase, it is known that a separation can be improved by increasing the surface area of the stationary phase.

In traditional liquid chromatography, a glass column is packed with stationary phase particles and mobile phase passes through the column, pulled only by gravity. However, when smaller stationary phase particles are used in the column, the pull of gravity alone is insufficient to cause the mobile phase to flow through the column. Instead, pressure must be applied. However, glass columns can only withstand about 200 psi. Passing a mobile phase through a column packed with 5 micron particles requires a pressure of about 2000 psi or more to be applied to the column. Today 5 to 10 micron particles are standard. Particles smaller than 5 microns are used for especially difficult separations or certain special cases. This process is denoted by the term "high pressure liquid chromatography" or HPLC.

HPLC has enabled the use of a far greater variety of types of particles used to separate a greater variety of chemical structures than was possible with large particle gravity columns. The separation principle, however, is still the same.

Certain components and operations of HPLC separation systems have been partially automated to facilitate the traditional partition-based separations. An example is the HSM control system provided by Hitachi with their HPLC chromatography apparatus. In using these controls, a chromatography expert manually inputs detailed instructions to an autosampler to obtain a specific sample for separation, detailed simple instructions to proportioning valves to effect a desired solvent gradient, and specific temperature instructions to a column oven. The control system automatically implements these instructions to effect a HPLC separation.

An HPLC-based ion pairing chromatographic method, reverse phase ion pairing chromatography was recently introduced to effectively separate mixtures of double stranded polynucleotides in general, and DNA in particular, wherein the separations are based on base pair length (U.S. Pat. No. 5,585,236 to Bonn (1996); Huber, et al., *Chromatographia* 37:653 (1993); Huber, et al., *Anal. Biochem.* 212:351 (1993)). These references and the references contained therein are incorporated herein in their entireties. The term "Matched Ion Polynucleotide Chromatography" (MIPC) is defined herein and applied to this method because the mechanism of separation was found to be based on binding and release of the DNA from the separation surfaces rather than traditional partitioning. MIPC separates DNA fragments on the basis of base pair length and is not limited by the deficiencies associated with gel based separation methods.

Matched Ion Polynucleotide Chromatography, as used herein, is defined as a process for separating single and double stranded polynucleotides using non-polar separation media, wherein the process uses a counter-ion agent, and an organic solvent to release the polynucleotides from the separation media. MIPC separations are complete in less than 10 minutes, and frequently in less than 5 minutes.

As the use and understanding of MIPC developed, it was discovered that when MIPC analyses were carried out at a partially denaturing temperature, i.e., a temperature sufficient to denature a heteroduplex at the site of base pair mismatch, homoduplexes could be separated from heteroduplexes having the same base pair length (U.S. Pat. No. 5,795,976; Hayward-Lester, et al., *Genome Research* 5:494 (1995); Underhill, et al., *Proc. Nati. Acad. Sci. USA* 93:193 (1996); Doris, et al., *DHPLC Workshop*, Stanford University, (1997)). These references and the references contained therein are incorporated herein in their entireties. Thus, the use of Denaturing HPLC (DHPLC) was applied to mutation detection (Underhill, et al., *Genome Research* 7:996 (1997); Liu, et al., *NucleicAcid Res.*, 26;1396 (1998)).

DHPLC can separate heteroduplexes that differ by as little as one base pair. However, separations of homoduplexes and heteroduplexes can be poorly resolved. Artifacts and impurities can also interfere with the interpretation of DHPLC separation chromatograms in the sense that it may be difficult to distinguish between an artifact or impurity and a putative mutation (Underhill, et al., *Genome Res.* 7:996 (1997)). The presence of mutations may even be missed entirely (Liu, et al., *Nucleic Acid Res.* 26:1396 (1998)). The references cited above and the references contained therein are incorporated in their entireties herein.

The accuracy, reproducibility, convenience and speed of DNA fragment separations and mutation detection assays based on DHPLC have been compromised in the past because of DHPLC system related problems. Important aspects of DNA separation and mutation detection by HPLC and DHPLC which have not been heretofore addressed include the treatment of materials comprising chromatography system components; the treatment of materials comprising separation media; solvent pre-selection to minimize methods development time; optimum temperature pre-selection to effect partial denaturation of a heteroduplex during MIPC; and optimization of DHPLC for automated high throughput mutation detection screening assays. These factors are essential in order to achieve unambiguous, accurate, reproducible and high throughput DNA separations and mutation detection results.

A need exists, therefore, for an HPLC system which can separate DNA fragments based on size differences, and can also separate DNA having the same length but differing in base pair sequence (mutations from wild type), in an accurate, reproducible, reliable manner. Such a system should be automated and efficient, should be adaptable to routine high throughput sample screening applications, and should provide high throughput sample screening with a minimum of operator attention.

The MIPC separation process differs from the traditional HPLC separation processes in that the separation is not achieved by a series of equilibrium separations between the mobile phase and the stationary phase as the liquids pass through the column. Instead, the sample is fed into the column using a solvent strength which permits the sample dsDNA to bind to the separation media surface. Strands of a specific base pair length are removed from the stationary phase surface and are carried down the column by a specific solvent concentration. By passing an increasing gradient of solvent through the sample, successively larger base pair lengths are removed in succession and passed through the column. The separation is not column length or stationary phase area dependent.

This MIPC process is temperature sensitive, and precise temperature control is particularly important in the MIPC separation processes described in co-pending U.S. patent application Ser. No. 09/129,105 filed Aug. 4, 1998, for example.

In DMIPC, precise temperature control is required for maintaining both mobile and stationary phases at a partially denaturing temperature, that is, a temperature at which mismatched DNA present at the mutation site of a heteroduplex strand will denature but at which the matched DNA will remain bound into the double strand.

The application of the Matched Ion Polynucleotide Chromatography (MIPC) under the partially denaturing conditions used for separating heteroduplexes from homoduplexes in mutation detection is hereafter referred to as DMIPC.

The MIPC systems have introduced system operation requirements which cannot be satisfied with existing control systems. Sample trays with an increased number of wells have been introduced, requiring corresponding detailed autosampler instructions for extracting a separation aliquot of each of the samples. More complex and varied solvent concentration and gradient instructions are required. More precise temperature control is essential, and in some operations, aliquots from the same sample are to be separated at different preset temperatures. The MIPC system will be used to isolate pure fractions, each having a single base pair size; these are needed for PCR or cloning amplification techniques. This requires use of a fragment collector operating in coordination with the MIPC separation process. Furthermore, the expanding application of MIPC separation processes requires the system to be operable by a trained technician rather than a chromatography expert.

U.S. Pat. No. 5,772,889 and co-pending applications Ser. Nos. 09/081,040, 09/183,123, 09/183,450 describe processes for removing or avoiding metal cations from apparatus, separation media, and solutions to obtain maximally effective separation of DNA fragments. If these precautions and procedures are followed, the separation columns can be used for more than 1000 separation cycles before significant loss of effectiveness and efficiency can be observed and the routine cleanup procedures fail to fully restore the column. Ultimately, the column efficiency decreases.

DNA separations to prepare materials for cloning or PCR should be free from cross-contamination from prior separations conducted on the separation system and column. A method is needed to insure removal of all DNA residues from the column in preparation for separation of purified DNA fragments for amplification.

SUMMARY OF THE INVENTION

It is an object of this invention to provide a cleaning system and procedure for regenerating or recovering a MIPC column which has become less effective because of extensive use.

It is a further object of this invention to provide a column regenerating system which does not require removal of the separation column to carry out the cleaning procedure.

It is a further object of this invention to provide an in situ cleaning method for insuring removal of DNA residues prior to separations designed to produce purified fractions for cloning or PCR amplification.

In summary, the apparatus of this invention effecting base pair length separations of DNA fragments by matched ion paired chromatography comprises a separation column containing separation media having non-polar DNA separation surfaces, separation solution supply means, and a separation solution conduit communicating with the separation column and the separation solution supply means, and a cleaning solution valve means positioned in the separation solution conduit for injecting cleaning solution into the separation solution conduit. The cleaning solution valve can be a rotary valve.

One embodiment of this apparatus for effecting base pair length separations of DNA fragments by matched ion paired chromatography comprises a separation column containing separation media having non-polar DNA separation surfaces, a cleaning solution injection valve having a DNA separation solvent inlet conduit port communicating with a separation solvent supply means, a cleaning solution port communicating with a cleaning solution supply means, a cleaning solution loop, a waste outlet port, and an outlet port communicating with the separation column. The cleaning solution loop communicates with the cleaning solution supply means and the waste outlet port in a first position, whereby the cleaning solution loop can be filled with cleaning solution. The cleaning solution loop communicates with the separation solvent supply means and the outlet port communicating with the separation column in a second position, whereby cleaning solution in the cleaning solution loop can be displaced by separation solvent through the outlet port communicating with the separation column.

In summary, a process of this invention for cleaning the non-polar DNA separation surfaces with the above apparatus comprises interrupting the flow of separation solvent with a block of cleaning solution injected into the flow of separation solution passing to the column, the cleaning solution containing agent which removes accumulated residues from the non-polar surface. The cleaning solution can have an alkaline pH, for example a pH of from 8 to 13. The cleaning solution can contain a chelating agent and can contain an organic solvent. The above apparatus can also be used in the separation of RNA.

BRIEF DESCRIPTION OF THE DRAWINGS

FIG. 9 (b) illustrates a chromatogram from a MIPC separation of a standard mixture of DNA fragments after a column cleaning procedure.

DETAILED DESCRIPTION OF THE INVENTION

The objects of this invention are provided in the improved MIPC apparatus and method of this invention. As described in earlier, copending and commonly assigned applications, MIPC separation processes can be applied to effect size-based separation of DNA fragments, mutation detection, DNA fragment purification, PCR process monitoring and other novel processes. This invention is directed to the system with a cleaning solution injection capability for restoring the separation column in place in the system and to remove any DNA residues from the column between separation processes.

In the following description, the term "mutation separation profile" includes a DMIPC separation chromatogram which shows the separation of heteroduplexes from homoduplexes. Such separation profiles are characteristic of samples which contain mutations or polymorphisms and have been hybridized prior to being separated by DMIPC.

A "homoduplex" is defined herein to mean, a double stranded DNA fragment wherein the bases in each strand are complimentary relative to their counterpart bases in the other strand.

A "heteroduplex" is defined herein to mean a double stranded DNA fragment wherein at least one base in each strand is not complimentary to at least one counterpart base in the other strand. This can be due to a mismatched base or a deletion. Since at least one base pair in a heteroduplex is not complimentary, it takes less energy to separate the bases at that site compared to its fully complimentary base pair analog in a homoduplex. This results in the lower melting temperature at the site of a mismatched base of a hetroduplex compared to a homoduplex.

The term "hybridization" refers to a process of heating and cooling a dsDNA sample, e.g., heating to 95° C. followed by slow cooling. The heating process causes the DNA strands to denature. Upon cooling, the strands re-combine into duplexes in a largely statistical fashion. If the sample contains a mixture of wild type and mutant DNA, then hybridization will form a mixture of hetero- and homoduplexes.

Figure 1:
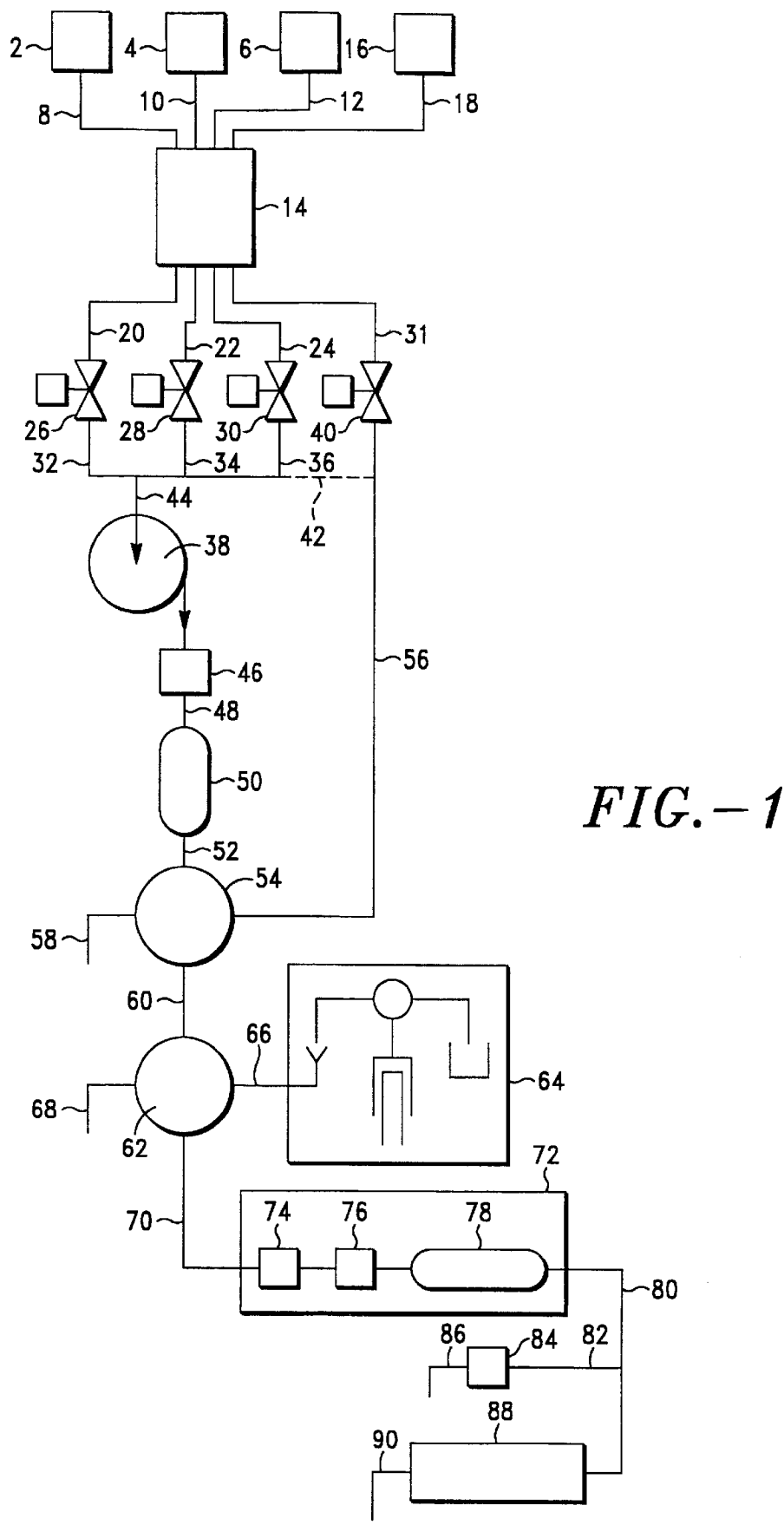
FIG. 1 is a schematic representation of a single column MIPC system using valves and valve controls to establish elution solvent gradients.

FIG. 1 is a schematic representation of a MIPC system. Chromatographic solutions such as solvents, counter-ions, and other solutions to be mixed with the solvents are maintained in solvent container 2, carrier liquid container 4, and auxiliary liquid (e.g., a co-solvent) container 6 having respective solvent transport tubing 8, carrier transport tubing 10 and auxiliary liquid transport tubing 12 communicating therewith and leading to degasser 14.

Figure 2:
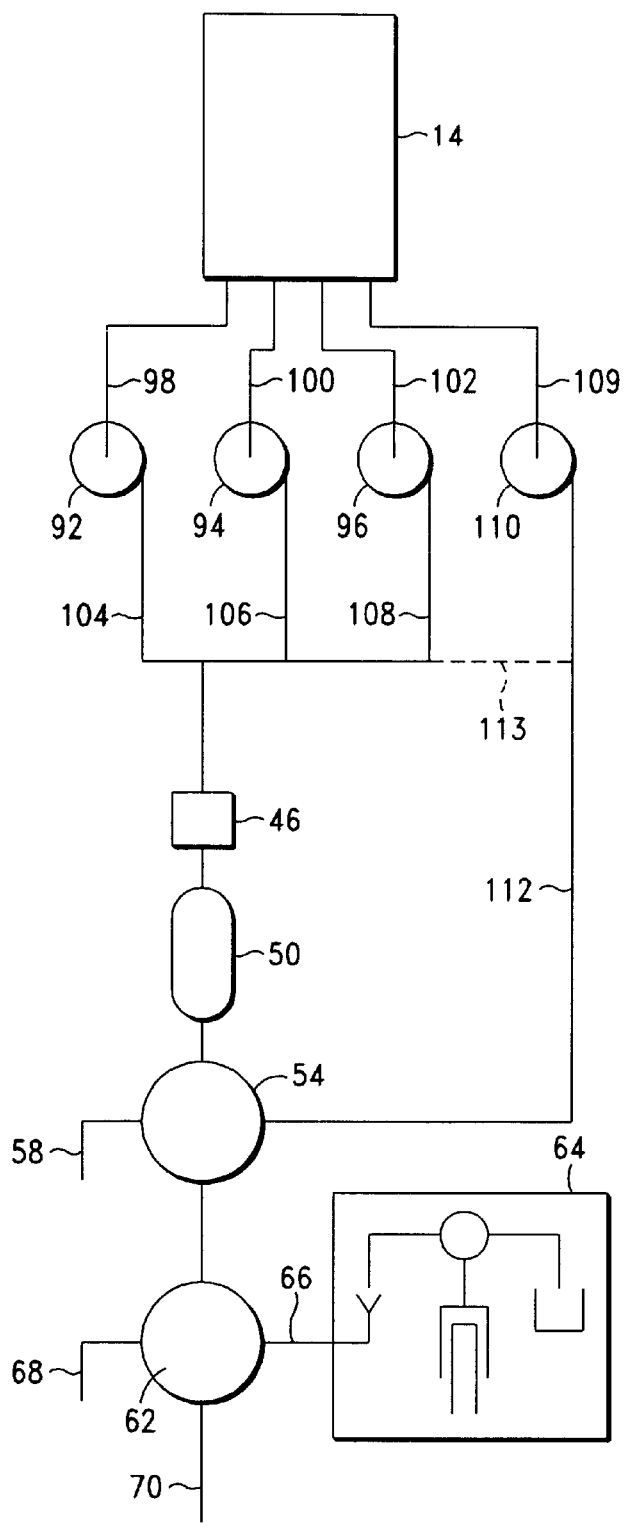
FIG. 2 is a partial schematic representation of a pump system for establishing elution solvent gradients.

Column cleaning solution is contained in cleaning solution container 16 which likewise has a cleaning solution transport conduit 18 communicating therewith leading to the degasser 14. In this embodiment, the cleaning solution can flow by gravity pressure if the container 16 is elevated above the degasser 14 and injection valve 54. Alternatively, a vacuum can be applied to the waste conduit 58 or a pump as shown in FIG. 2 can be provided to achieve cleaning solution flow.

Degassed solvent conduit 20, degassed carrier liquid conduit 22, and degassed auxiliary liquid conduit 24 leading from the degasser 14 communicate with respective solvent proportioning valve 26, carrier liquid proportioning valve 28, and auxiliary liquid proportioning valve 30. Conduits 32, 34, and 36 lead from respective proportioning valves 26, 28 and 30 to the intake of the pump 38. The degasser 14 removes dissolved gases from the liquids. Removal of dissolved oxygen in particularly important because its presence increases the risk of oxidizing ferrous or other oxidizable metals in the system components and thus introducing the corresponding cations into the liquid.

The cleaning solution transport conduit 31 leads to a cleaning solution valve 40. An optional cleaning solution conduit 42 leads from the valve 40 and communicates with the inlet of the pump 38.

The openings of valves 26, 28 and 30 accurately set the relative ratios of the solvent or solvents to carrier liquid, a most important part of this system because the size-based DNA separation by MIPC is a function of solvent concentration. As will be described in regard to the various DNA fragment separation processes, the slope of the solvent gradient as a function of time is changed during the separation process, and the most critical phase may require a very precise gradient, or for some processes, a highly precise isocratic (constant solvent concentration) composition. The settings of the valves 26, 28 and 30 are established by conventional valve actuators which can be remotely set by signals to a conventional valve control device. As will be described in greater detail hereinafter, the control system of this invention provides computer controlled instructions which establish the settings of valves 26, 28 and 30 to precise flow values at appropriate times during the operation of the system.

In a similar manner, the control system of this invention provides computer controlled instructions to establish the operational parameters of the pump 38, such as the off/on status of the pump and the pressure or flow rate settings of the pump.

Pump outflow conduit 44 communicates with the in-line mixer 46, directing the liquid flow through the mixer 46 for thorough mixing of the components. Mixed liquid outflow conduit 48 communicates with guard column 50 to treat the mixed liquid to remove multivalent metal cations and other contaminants which would interfere with the separation of DNA fragments. Guard column 50 can contain a cation exchange resin in sodium or hydrogen form for removal of multivalent metal cations by conventional ion exchange. Conduit 52 communicates with the outlet of the guard column and an inlet port of a cleaning solution injector valve 54. Cleaning solution supply conduit 56 connects valve 40 with the cleaning solution injector valve 54, and waste outlet conduit 58 leads to waste. Conduit 60 leads from the cleaning solution injector valve 54 to the sample injection valve 62.

Sample aliquot selector 64 communicates with sample injector valve 62 through sample conduit 66. Waste conduit 68 leads from the injector valve and removes waste liquids. Details about the sample aliquot selector 64 are provided in greater detail hereinafter with respect to FIG. 3, and details about the cleaning solution and sample injector valves 54 and 62 and their operation are presented in greater detail hereinafter with regard to FIGS. 4–8.

In the injector valve 62, the sample is introduced into a stream of solvent and carrier liquid passing through the valve from conduit 60. Sample conduit 70 communicates with an outlet port of injector valve 62 and with the column prefilter 74 in the air bath oven 72. The capillary tubing coil 76 communicates with the prefilter 74 and the inlet of separation column 78. The extended length of the capillary coil 76 allows ample heat to pass from the heated oven air into the liquid passing through the coil, bringing the liquid within ±0.05° C. of a selected temperature. The oven 72 establishes this temperature uniformity in the prefilter 74, coil 76, and separation column 78.

The separation column 78 is packed in a conventional column construction with beads having a unique separation surface which effects a size-based separation of DNA fragments in the presence of a matched counter-ion by the MICP process. The separation process and details about the beads are described in detail hereinafter. A stream (eluant) containing base pair length size-separated DNA fragments passes from the separation column 78 through eluant conduit 80.

Analyzer conduit 82 communicates with conduit 80 to remove a fraction of liquid therefrom for continuous measurement with an analyzer cell 84. The analyzer cell can be a conventional UV absorption measurement device which measures the UV absorption level of the native DNA fragment structures in the liquid. The absorption level is a function of the concentration of the DNA fragments in the liquid being tested.

Alternatively, if the DNA can be labeled with a fluorescent marker, the analyzer continuously measuring the level of the fluorescent marker in the liquid by detecting the emission level at the frequency most appropriate for the marker. It will be readily apparent that any analyzing system capable of continuously measuring a characteristic of the liquid which is a function of the concentration of the DNA fragments therein is suitable and intended to be within the scope of this invention. Waste conduit 86 removes the tested liquid.

The remaining portion of the eluant passes to the fragment collector 88. In the fragment collector 88, selected portions of the eluant containing a separated DNA fraction are collected in a vials for later processing or analysis. Uncollected fractions are removed through waste conduit 90.

The DNA separation process is impaired by the presence of multivalent cations. In the above description, the liquid flow system is described as a series of conduits. The conduits are capillary tubing selected to avoid introduction of multivalent cations into the liquids. The preferred capillary tubing materials are titanium and PEEK. For similar reasons, the other components of the system are preferably made of titanium or PEEK or have the surfaces exposed to the liquid coated with PEEK to protect them from oxidation and prevent the introduction of multivalent cations into the liquid. Stainless steel can also be used provided it has been treated to remove all oxidized surface materials and the solutions contacting the stainless steel surfaces are free of dissolved oxygen.

FIG. 2 is a partial schematic representation of a pump system for establishing elution solvent gradients. This system relies on proportioning pumps to control the ratio of solvents to carrier liquids. The inlets of proportioning pumps 92, 94 and 96 by way of their respective supply conduits 98, 100, and 102 communicate with the degasser 14, and by way of their respective outlet conduits 104, 106 and 108 communicate with the inline mixer 46. A pump 110 supplies cleaning liquid from conduit 109 to the system through optional conduit 112. An optional conduit 113 can lead from conduit 112 and communicate with the in-line mixer 46.

Figure 3:
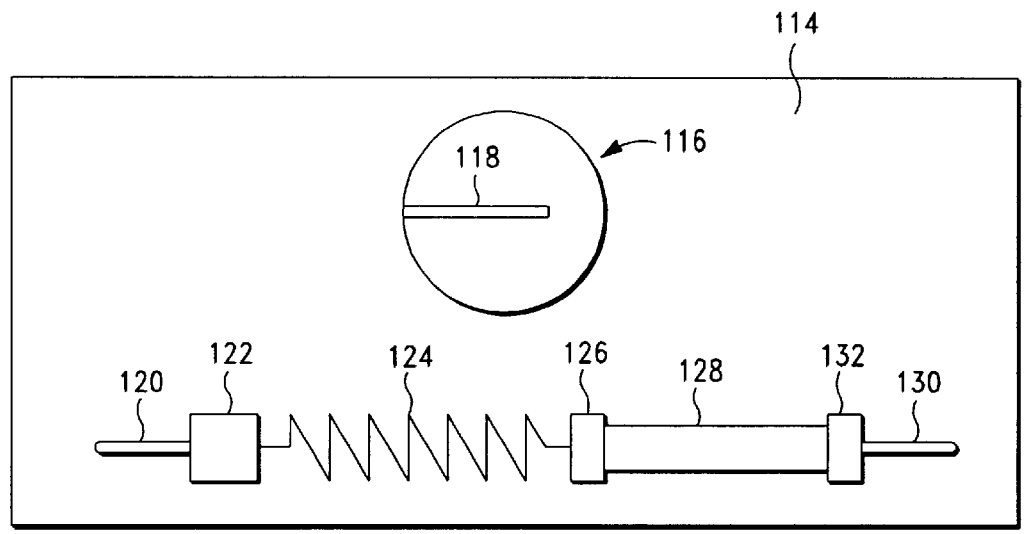
FIG. 3 is a front view of the separation column and solution preheat system in an air-bath oven.

FIG. 3 is a front view of the separation column and solution preheat system in an air-bath oven. The process compartment in the embodiment shown in FIG. 3 is divided from the heating compartment by backwall 114 in which air exhaust port 116 is positioned. A metal bar 118 enclosing a temperature sensor such as a thermocouple or thermister is positioned in the port 116 to measure the temperature of the air passing through the port.

Capillary tubing 120 leads from the sample injector (not shown) to a prefilter 122. Prefilter 122 is an inline filter or guard cartridge such as described in U.S. Pat. No. 5,772,889. It removes contaminants from the incoming liquid. An elongated coil 124 of capillary tubing has an inlet end communication with prefilter 122 for receiving process liquid therefrom. The elongated coil 124 has an outlet end communicating with the inlet end 126 of a separation column 128. Separation column 128 contains MIPC separation media described in U.S. Pat. No. 5,585,236 and co-pending U.S. patent applications Ser. Nos. 09/058,580, 09/058,337, 09/183,123, 09/183,450. Outlet tubing 130 leads from the outlet end 132 of the separation column 128 to detector 76 (FIG. 1).

The coil 124 is a liquid heating coil made of a DNA compatible, multivalent cation free tubing such as titanium or PEEK described in U.S. Pat. No. 5,772,889 and application Ser. No. 09/081,040. The length and diameter of tubing used is any length which is sufficient to enable liquid passing therethrough to reach the equilibrium temperature of air in the processing compartment. A tubing length of from 6 to 400 cm and a tubing ID of from 0.15 to 0.4 mm is usually sufficient. Since the length of tubing 124 does not degrade the separation of components achieved by the system, the length can be selected based on the length required to achieve effective heating of the process liquids.

Air from the processing compartment containing the column 128 passes through the opening 116 in wall 114, through a heater/fan system for temperature adjustment. The adjusted air recycles back to the processing compartment.

The heating coil 124 provides a fluid temperature accuracy within the range of ±0.2° C. and reduces the temperature equilibrium time between temperature settings to below 5 minutes for temperature changes of 5° C. and below 2 minutes for temperature changes for upto 1° C.

Figure 4:
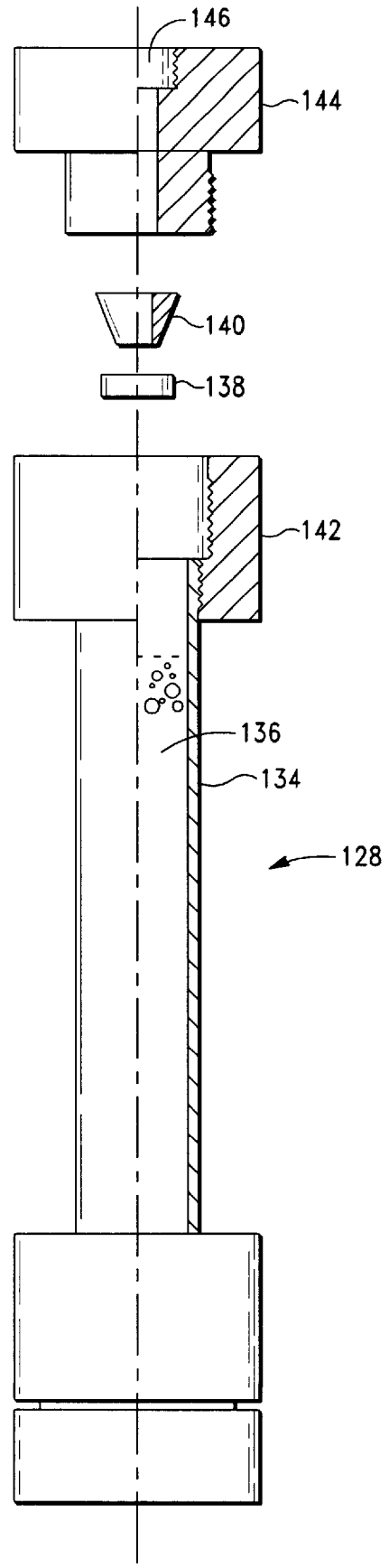
FIG. 4 is a representation of the physical structure of a representative separation column.

FIG. 4 is a partially exploded representation of the physical structure of a representative separation column. The column comprises a column tube 134 with external threads on both ends. The tube is filled with separation media 136. A frit 138 is held against the upper surface of the separation media by the frit plug 140. An internally threaded coupling 142 is secured to the end of the tube 134 and receives the frit 138 and frit plug 140. The internally threaded coupling 142 receives the externally threaded coupling 144 in a threaded engagement. The externally threaded coupling 144 has an internally threaded end receptor 146 for receiving a capillary tubing end coupler (not shown).

The separation media 136 are organic polymer materials or inorganic materials having the requisite structure and non-polar surfaces. Suitable materials are described in copending, commonly assigned patent applications Ser. No. 09/183,123 filed Oct. 20, 1998 and Ser. No. 09/183,450 filed Oct. 20, 1998.

During repeated use, the separation media 136 becomes less active because of a gradual fouling of the media surface by solutions and samples they contact during use. Furthermore, slight residues of DNA fragments may escape removal during the normal clean-up phase of the process during which a concentrated driving solvent is passed through the column. The process and system of this invention applies highly effective cleaning solutions to the surface of the separation media to remove these residues and contaminants, thereby restoring the separation media to a fully effective state.

Figure 5:
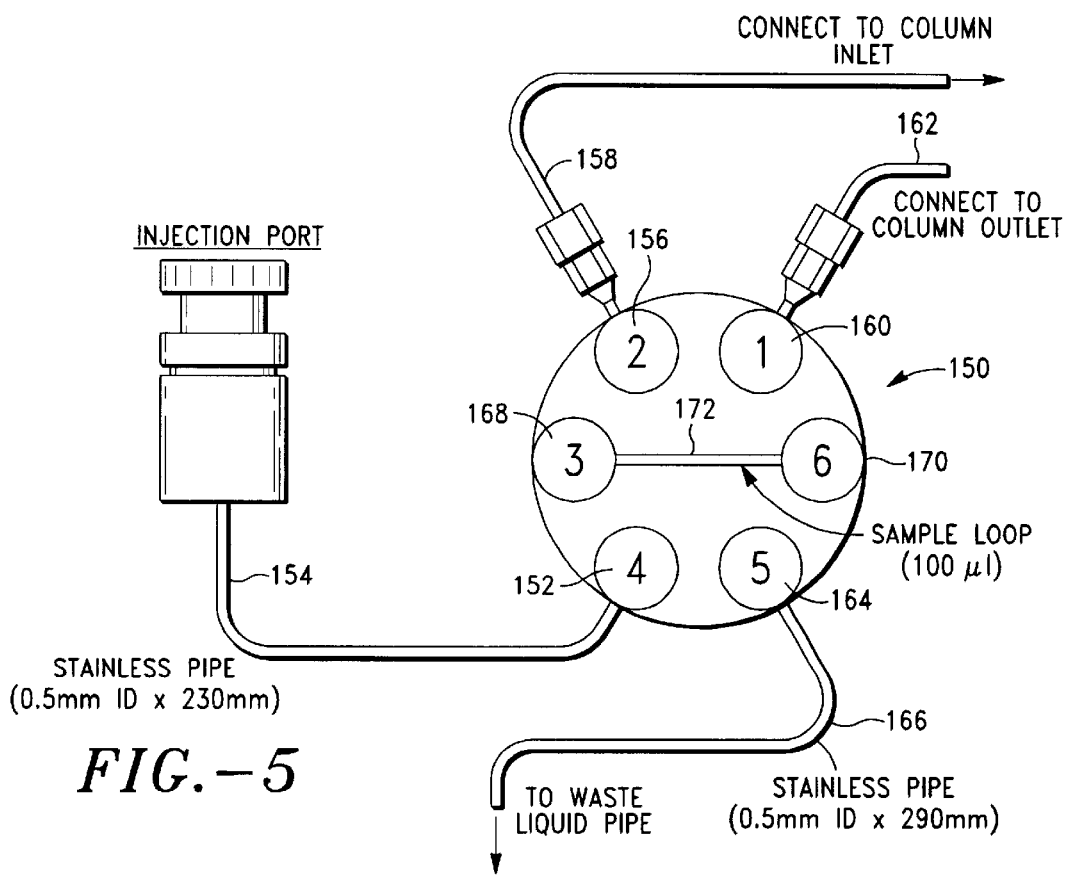
FIG. 5 is schematic representation of an injection valve used in the MIPC system.

FIG. 5 is schematic representation of a cleaning solution injection valve 54 shown in FIG. 1. The same structure can be used in the sample injection valve 62 shown in FIG. 1. The injection valve 150 is a six-port, rotary valve operated by a conventional valve motor such as a stepper motor (not shown), for example. The valve has six external ports permanently connected to inlet and outlet conduits. External port 152 is connected with an injection line 154 for receiving the cleaning solution. External port 156 is connected with an column supply conduit 158 communicating with the separation column 78 (FIG. 1). External port 160 is connected with an inlet conduit 162 communicating with the outlet of pump 38 (FIG. 1). External port 164 is connected with a waste conduit 166. Opposed outlet ports 168 and 170 communicate with the opposed cleaning solution inlet and outlet ends of a cleaning solution loop 172.

Figures 6, 7:
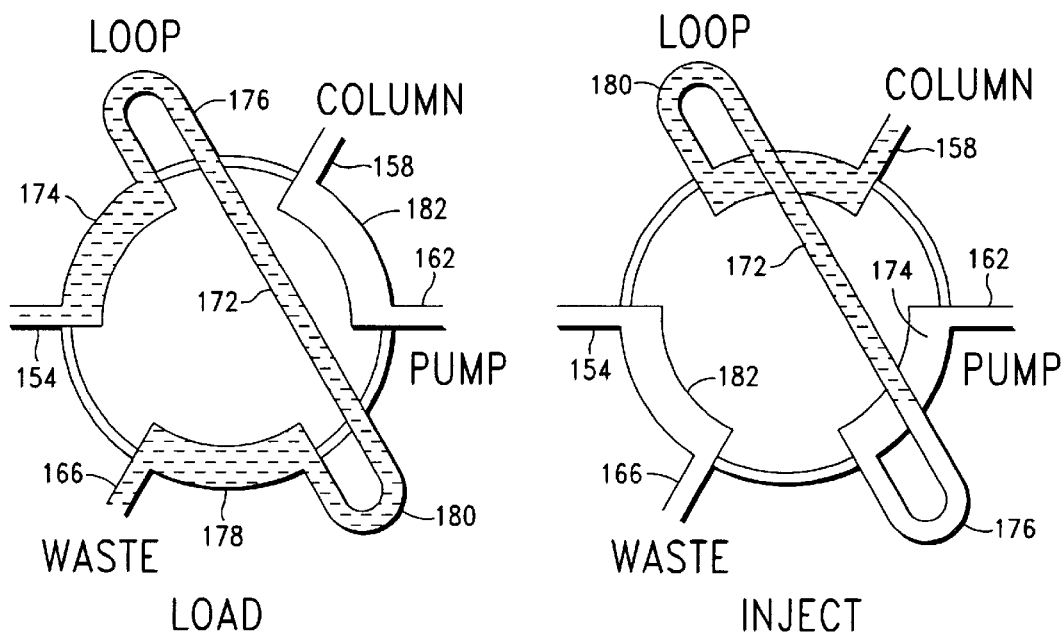
FIG. 6 is a schematic representation of an injection valve in the filled loop load position.
FIG. 7 is a schematic representation of an injection valve in the filled loop injection position.

The connections between the external ports and internal passages, and their operation in the cleaning solution injector valve 54 are described in FIGS. 6 and 7. FIGS. 6 and 7 describe the use of the valve for filled loop injection, the mode used when cleaning liquid is injected. FIG. 6 is a schematic representation of an injection valve in the cleaning solution load position, and FIG. 7 is a schematic representation of the injection valve in the injection position. In the load position shown in FIG. 6, a first internal passageway 174 of the valve 150 connects the first end 176 of loop 172 with the cleaning solution injection line 154, and a second internal passageway 178 connects the second end 180 of loop 172 with the waste conduit 166. A third internal passageway 182 connects the pump outlet conduit 162 with the conduit 158 to the separation column 78. While cleaning solution from the injection port 154 is introduced into the sample loop 172 through passageway 174, any surplus or liquid in the loop 172 is expelled to the exhaust conduit through passageway 178. Simultaneously, process solutions flow from the pump conduit 162 to the separation column 70 through third conduit 182.

Rotation of the valve 150 to the injection position shown in FIG. 7 moves the internal passageways to establish a different set of connections with the inlet and outlet conduits. Second passageway 178 connects one end 180 of the loop 172 with the conduit 158 leading to the separation column, and the first passageway 174 connects the other end 176 of the loop 172 with the inlet conduit 162 leading to the pump. Solution from the pump enters passageway 174 and passes through the loop 172, expelling cleaning solution into the conduit 158 leading to the column and continues to rinse the loop, carrying any residue into the column conduit 158. Meanwhile passageway 182 connects the cleaning solution injection conduit 154 to waste, permitting passage of cleaning solution, if desired, through passageway 182.

The procedures described herein have focused on restoration of the separation media surfaces by injection of a cleaning solution with injection valve 54.

The last phase of each separation includes passing an aqueous solution with a maximum (e.g., 25 percent) concentration of stripping solvent from reservoir 4 to remove any remaining DNA from the surface of the separation media and prepare the column for the next run. The settings of valves 26, 28 and 30 are then returned to the start position, that is, the settings required to effect binding of the next sample DNA fragments to the separation media surface. As an alternative procedure, at the end of each run cleaning solutions from reservoir 16 can be routinely injected into the system by valve 54 to regenerate and clean the separation media surfaces in the separation column 76. While this alternative procedure is underway, valves 26, 28 and 30 can be reset to the start position. This can decrease the time of each separation cycle and increase the effective throughput of the column system.

This procedure provides a reliable injection of a volume of cleaning solution into the conduit leading to the separation column 78 (FIG. 1), the liquid passing through the prefilter 74, temperature regulating coil 76 before it reaches the separation column 78, cleaning all surfaces with which it makes contact from the injector through the remainder of the system.

The cleaning solutions passed through the separation column can be any material which will effectively remove the accumulated surface residue and any residual DNA materials from the separation column, prefilter, and all capillary conduit surfaces downstream of the injector. The cleaning solution must not attack or deteriorate any of the surfaces with which it makes contact. Suitable cleaning solutions and the materials they remove from the column are shown in Table A.

TABLE A

| Cleaning Solution Reagent | Materials removed: |
| --- | --- |
| Methanol, acetonitrile and organic solvents in general | Organic contaminants, proteins, peptides, DNA residues and genomic DNA, for example. |
| Tetrasodium EDTA (0.1–500 mM) and other alkali metal and ammonium salts of chelating agents. Heated solutions can also be used. | Multivalent metal cations, proteins, peptides and genomic DNA |
| Nitric acid (5–35%) | Metal ions, metals, basic contaminants, and the like. This will also passivate (remove metal ion contaminants from the surface of) stainless steel components of the system downstream of the injection valve. |

TABLE A-continued

| Cleaning Solution Reagent | Materials removed: |
| --- | --- |
| Sodium hydroxide and other alkali hydroxides and strong bases (organic and/or inorganic). | Genomic DNA, proteins, peptides, and acidic contaminants |

For removing DNA residues, sodium EDTA solutions having a pH up to 13 and which can be heated are particularly useful for injection, although lower pH's are advised if the separation media is vulnerable to alkaline solutions, e.g., silica based particles and the like.

Larger DNA contaminants such as genomic DNA cannot be removed from the column with normal solvent solutions. These and other polynucleotide contaminants can be removed by digesting them into smaller fragments using enzymes such as RNase and DNAZAP (Ambion, Austin, Tex.). The digestion products are removed by flowing solvent solutions through the column.

All references cited herein are hereby incorporated by reference in their entirety.

This invention is further illustrated by the following specific but non-limiting examples wherein laboratory procedures which have been completed are presented in the past tense and procedures which have not been completed and are constructively reduced to practice in this application are presented in the present tense.

EXAMPLE 1

Cleaning a Contaminated Column with a Methanol Cleaning Agent

A separation gradient procedure was run on a separation column containing alkylated styrene-divinylbenzene beads (DNASepTM Column, 50 mm×4.6 mm ID, Transgenomic, Inc.) which had become ineffective during repeated use. The cause of the loss of separation efficiency is unknown.

Figure 8:
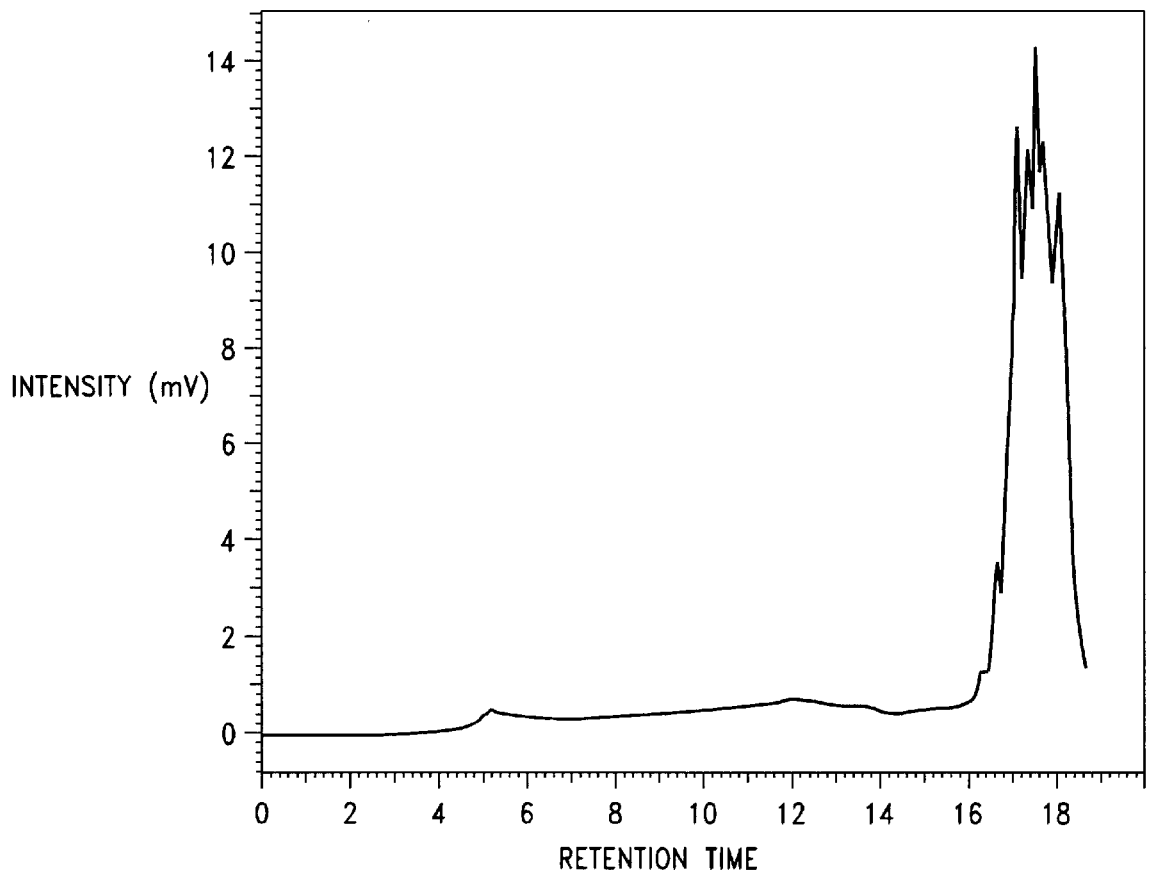
FIG. 8 illustrates a chromatogram from a MIPC separation gradient procedure run on a contaminated column.
Figure 9:
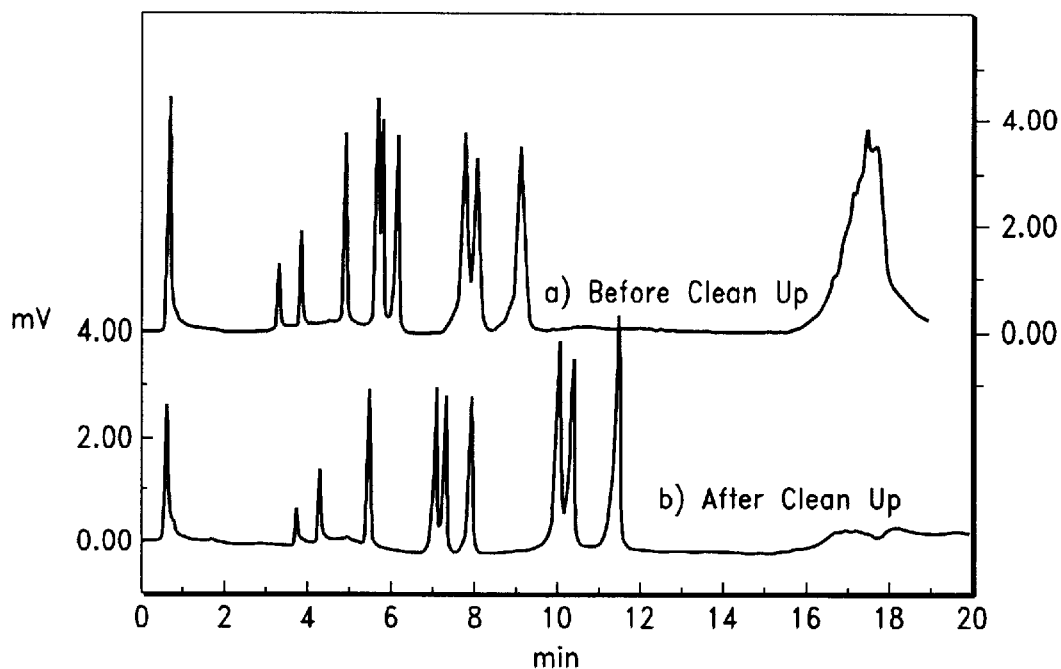
FIG. 9 (a) illustrates a chromatogram from a MIPC separation of a standard mixture of DNA fragments prior to a column cleaning procedure.

The column was tested three times, the detector output chromatograms for each test being shown in FIGS. 8 and 9. In the procedure producing FIG. 8, the column was tested by passing a standard solvent gradient through the column while detecting the output fractions. No DNA fragments were injected before this procedure, and any materials eluted represented contaminants in the column. In this procedure, the pH 7 mobile phase was comprised of component A, 0.1M triethylammonium acetate (TEM), and a component B, 0.1M TEM and 25% acetonitrile. The liquid passed through the column was formed by mixing proportions of Component B with Component A. Gradient conditions used in the separation shown were 35 to 55% B in three minutes, followed by 55 to 65% B in seven minutes, 65% B for 2.5 minutes, 100% B (column wash) for 1.5 minutes, and 35% B for 2 minutes to equilibrate the column for the next sample application. The backpressure was 2100 psi, the temperature 50° C., the UV detection at 260 nm, the flow rate of 0.75 mL/min. The chromatogram obtained during this elution is shown in FIG. 8. Even though no polynucleotide has been injected into the column, some materials on the column were eluted and appeared in the chromatogram as a peak at a retention time of 16 minutes.

The FIG. 9 chromatogram (a) Before Cleanup was obtained by performing a test separation procedure with a standard mixture of DNA fragments to determine the separating performance of the column. In this procedure, a 5 μL standard sample of 0.2 μg pUC18 HaeIII restriction digest, (No. D6293, Sigma/Aldrich Chemical Co.,) containing 80, 102, 174, 257, 167, 298, 434, 458, 587 base pair DNA fragments was injected onto the column and the fragments were eluted under gradient conditions. The pH 7 mobile phase comprised component A, 0.1M triethylammonium acetate (TEM) and component B, 0.1M TEM, 25% acetonitrile. Gradient conditions used in the separation were 35 to 55% B in three minutes, followed by 55 to 65% B in seven minutes, 65% B for 2.5 minutes, 100% B (column wash) for 1.5 minutes, and 35% B for 2 minutes to equilibrate the column for the next sample application. The back pressure was 2100 psi, temperature 50° C., UV detection at 260 nm, flow rate of 0.75 mL/min. The chromatogram of FIG. 9 was obtained. It may be noted that in addition to the peaks representing peaks corresponding to fractions of separated DNA, further column contaminate appeared as a peak at 16 minutes.

The column was then cleaned by flushing it with 100% methanol for 45 min (1 ml/min, T=50° C.) to remove contaminants from the stationary phase. After approximately 10–15 min the pressure increased from 120 bar to 240–260 bar. After another 20 min the pressure dropped again to 110–115 bar. It remained constant at 110 bar through the end of the washing procedure.

The FIG. 9 chromatogram (b) After Cleanup was obtained by repeating the separation procedure with the standard mixture of DNA fragments. A 5 μL standard sample of 0.2 μg pUC18 HaeIII restriction digest (No. D6293, Sigma/Aldrich Chemical Co.,) containing 80, 102, 174, 257,167, 298, 434,458, 587 base pair DNA fragments was injected onto the cleaned column. The pH 7 mobile phase comprised component A, 0.1M triethylammonium acetate (TEM) and component B, 0.1M TEM, 25% acetonitrile. Gradient conditions used in the separation shown in FIG. 9 were 35 to 55% B in three minutes, followed by 55 to 65% B in seven minutes, 65% B for 2.5 minutes, 100% B (column wash) for 1.5 minutes, and 35% B for 2 minutes to equilibrate the column for the next sample application. The back pressure was 2100 psi, temperature 50° C., UV detection at 260 nm, flow rate of 0.75 mL/min.

In the chromatogram of FIG. 9, the mV numbers are shown on the right side of the chromatogram to enable the FIG. 9(a) and FIG. 9(b) chromatograms to be presented together for easy comparison. A pronounced contaminant peak at 16 minutes is not visible, showing that the contaminant had been removed. Also the retention times of the fragments were increased to the times expected with an efficient column. Note the increase in distances between the peaks.

EXAMPLE 2

Cleaning a Contaminated Column with Heated Tetrasodium EDTA in Buffer Solution.

A contaminated separation column containing alkylated styrene-divinylbenzene beads (DNASepTM Column, 50 mm×4.6 mm ID, Transgenomic, Inc.) had become ineffective during repeated use. The cause of the loss of separation efficiency is believed to be multivalent ion and/or genomic DNA accumulations on the column.

The column was treated with 50% buffer B (0.1M TEM, 25% acetonitrile) and 50% buffer C (50 mM of tetrasodium EDTA) for 30 minutes at 1 ml/min at 75° C.

Figure 10:
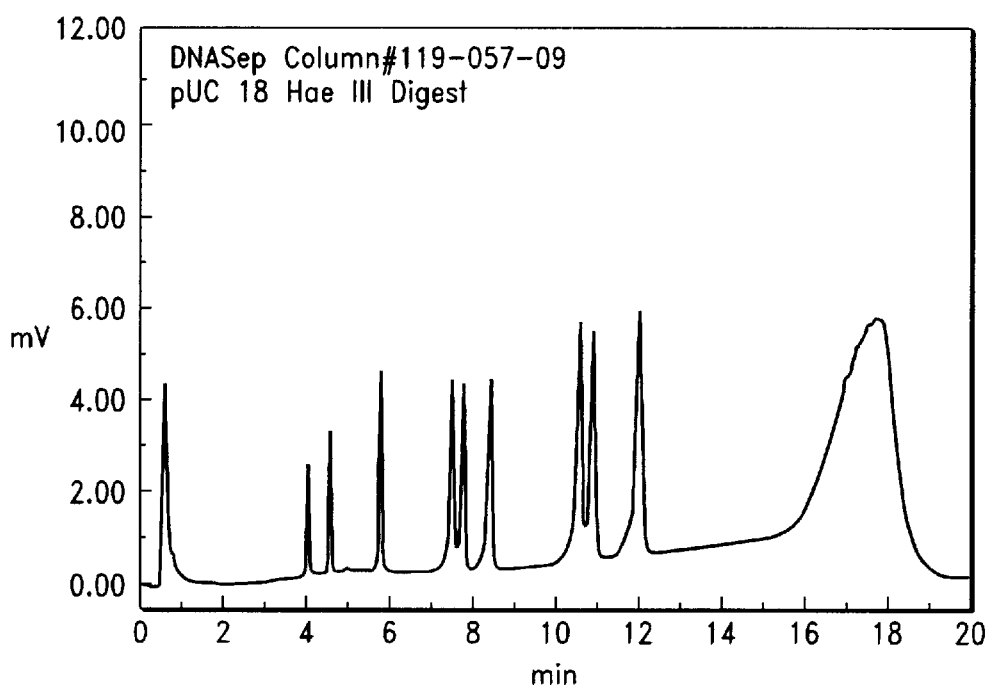
FIG. 10 illustrates a chromatogram from a MIPC separation of a standard mixture of DNA fragments using a column which was subjected to a cleaning treatment.

The column was then tested by a separation procedure using pUC 18 Hae lll digest as a standard test mixture of DNA fragments. A 5 μL standard sample of the digest was injected onto the column, and the fragments were eluted under gradient conditions to produce a reference chromatogram as shown in FIG. 10. The chromatogram shows the column had been restored to the original performance characteristics, demonstrating the cleaning procedure removed the contaminants.

EXAMPLE 3

Cleaning a Contaminated Column with an Acetonitrile Cleaning Agent

A separation gradient procedure was run on a separation column containing alkylated styrene-divinylbenzene beads (DNASep® Column, 50 mm×4.6 mm ID, Transgenomic, Inc.) which had become ineffective during repeated use. The cause of the loss of separation efficiency was unknown.

The column was tested by performing 60 injections of 5 µl, 1×Pfu buffer (Stratagene) containing TritonX-100 and BSA. In this procedure, the mobile phase was comprised of component A: 0.1M triethylammonium acetate (TEAA), component B: 0.1M TEAA and 25% acetonitrile, and component C: 75% acetonitrile in water. The liquid that passed through the column was formed by mixing proportions of the three components. Gradient conditions used in the separation shown are as follows:

| Time | % Component A | % Component B | % Component C |
|---|---|---|---|
| 0 | 65 | 35 | 0 |
| 0.5 | 35 | 65 | 0 |
| 1.5 | 35 | 65 | 0 |
| 1.6 | 0 | 0 | 100 |
| 2.1 | 0 | 0 | 100 |
| 2.2 | 65 | 35 | 0 |
| 4.2 | 65 | 35 | 0 |

The temperature was 50° C., the UV detection at 260 nm, and the flow rate was 0.75 mumin.

In this procedure, a 7 µL standard sample of 0.2 µg pUC18 HaeIII restriction digest, (No. D6293, Sigma/Aldrich Chemical Co.,) containing 80, 102, 174, 257, 267, 298, 434, 458, 587 base pair DNA fragments was injected onto the column and the fragments were eluted under the above gradient conditions.

Figure 11:
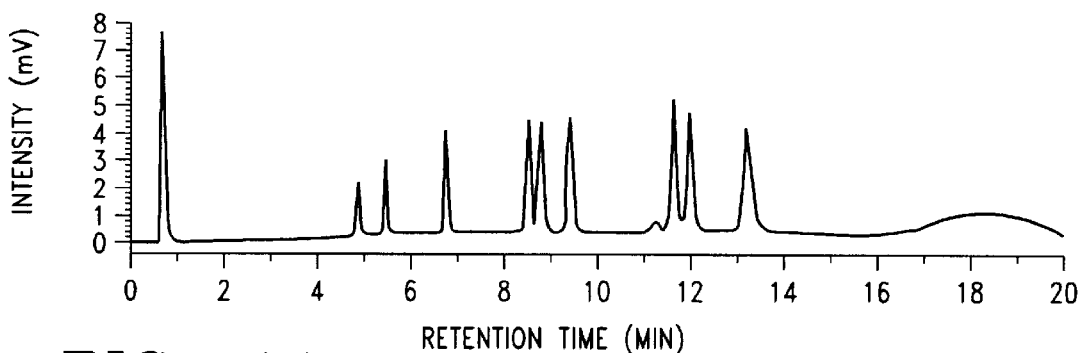
FIG. 11 is a separation profile of a standard mixture of DNA fragments using a 50 mm×4.6 mm ID MIPC column prior to injection of Pfu buffer.
Figure 12:
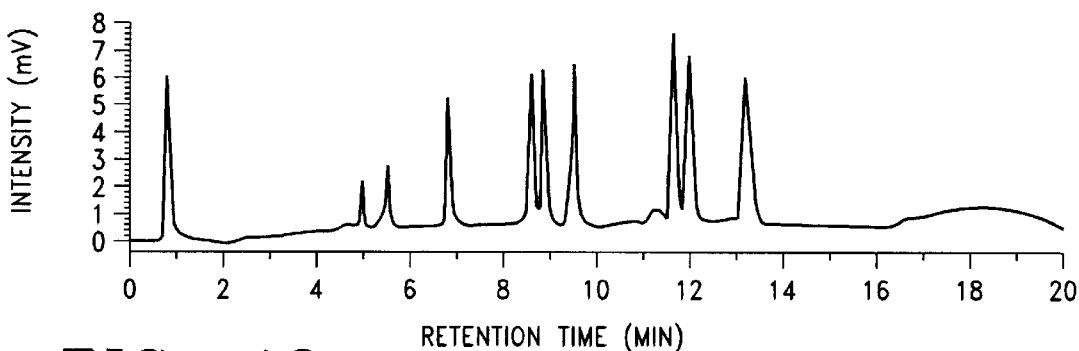
FIG. 12 is a separation profile of a standard mixture of DNA fragments using column used in FIG. 11 after repeated injections of Pfu buffer.
Figure 13:
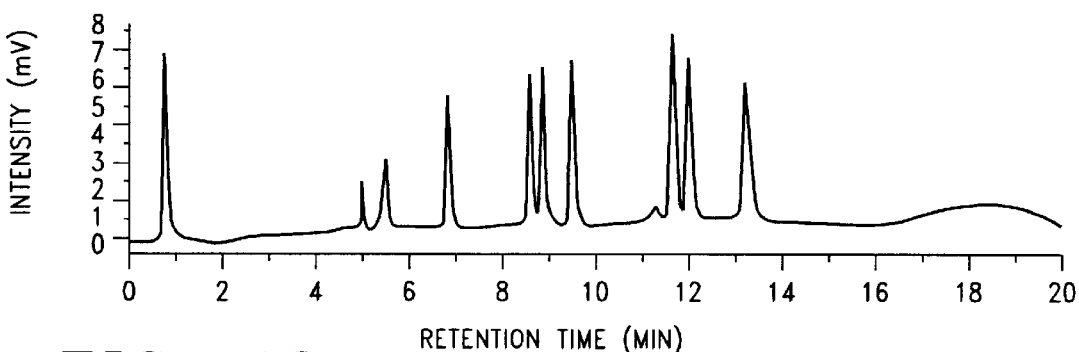
FIG. 13 is a separation profile of a standard mixture of DNA fragments using the column used in FIG. 12 after additional injections of Pfu buffer.
Figure 14:
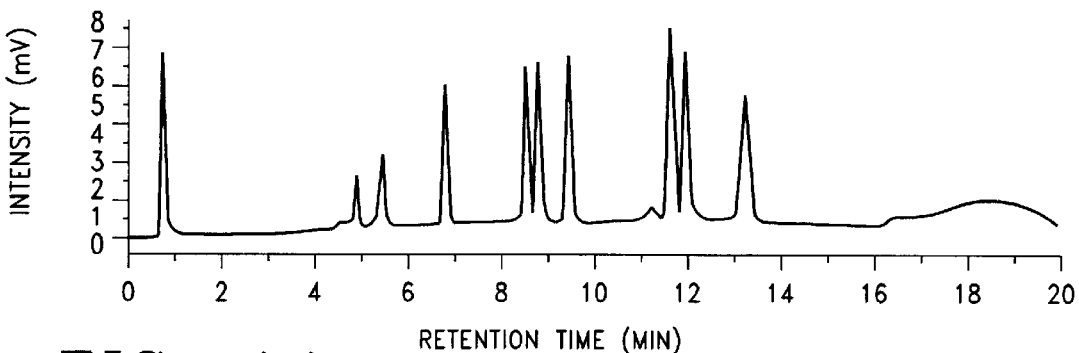
FIG. 14 is a separation profile of a standard mixture of DNA fragments using the column used in FIG. 13 after further injections of Pfu buffer.

FIG. 11 shows the separation of the pUC HaeIII digest before any injection of Pfu buffer onto the column. FIG. 12 through FIG. 14 show the separation of the pUC HaeIII digest after every 20 injections of Pfu buffer, for 3 sets of 20 injections, respectively.

In FIG. 11, the 587 bp fragment had a retention time of 13.11 minutes. FIG. 12 shows the same fragment appearing at 13.08 minutes after 20 Pfu buffer injections. FIG. 13 and FIG. 14 show the same fragment after 40 and 60 Pfu buffer injections, respectively. The retention times of these are both 13.11 minutes.

EXAMPLE 4

Cleaning a Contaminated Column with an Acetonitrile Cleaning Agent

A separation gradient procedure was run on a separation column containing alkylated styrene-divinylbenzene beads (DNASep® Column, 50 mm×4.6 mm ID, Transgenomic, Inc.) which had become ineffective during repeated use. The cause of the loss of separation efficiency was unknown.

The column was tested by performing 60 injections of 5 µL, 1×Pfu buffer (Stratagene) containing TritonX-100 and BSA. In this procedure, the mobile phase was comprised of component A: 0.1M triethylammonium acetate (TEM), component B: 0.1M TEM and 25% acetonitrile, and component C: 75% acetonitrile in water. The liquid that passed through the column was formed by mixing proportions of the three components. Gradient conditions used during the Pfu injections are as follows:

| Time (minutes) | % Component A | % Component B | % Component C |
|---|---|---|---|
| 0 | 50 | 50 | 0 |
| 0.5 | 47 | 53 | 0 |
| 4.0 | 40 | 60 | 0 |
| 5.0 | 0 | 0 | 100 |
| 5.5 | 0 | 0 | 100 |
| 5.6 | 50 | 50 | 0 |
| 8.6 | 50 | 50 | 0 |

The temperature was 50° C., the UV detection at 260 nm, and the flow rate was 0.9 mumin.

Figure 15:
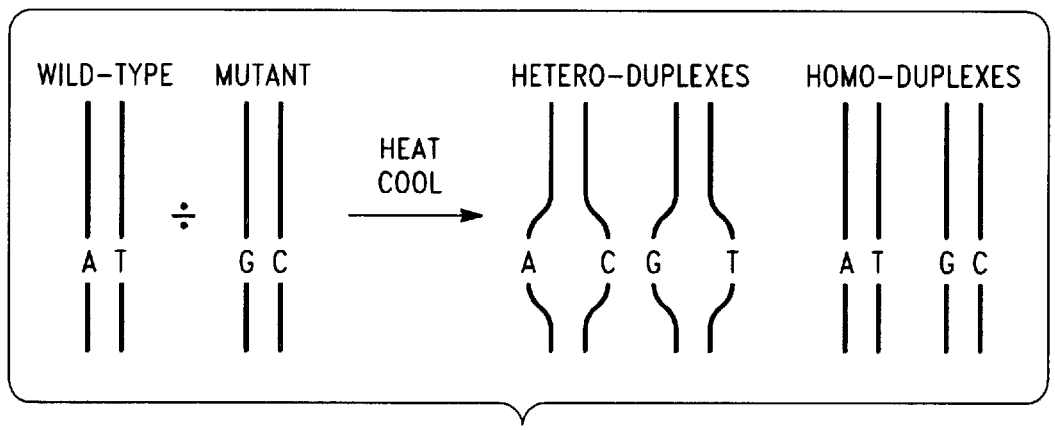
FIG. 15 shows a schematic representation of a hybridization to form homoduplex and heteroduplex.

In this procedure, a standard sample of a 209 base pair fragment (available as a mutation standard from Transgenomic, Inc.) from the human Y chromosome, locus DYS271 with an A to G mutation at position 168 was hybridized. The standard sample, containing a heterozygous mixture of 209 base pair homoduplex fragments wherein the mutant fragments contain a single base pair deviation from the wild type, was hybridized by heating and then cooling. The hybridization process created two homoduplexes and two heteroduplexes as shown schematically in FIG. 15.

5 µL of the hybridized sample was injected onto the column after each set of twenty Pfu injections, for total of three sets, and the 209 mutation standard fragments were eluted under the following gradient conditions:

| Time (minutes) | % Component A | % Component B | % Component C |
|---|---|---|---|
| 0 | 50 | 50 | 0 |
| 0.5 | 47 | 53 | 0 |
| 4.0 | 40 | 60 | 0 |
| 5.5 | 0 | 0 | 100 |
| 6.5 | 50 | 50 | 0 |
| 8.4 | 50 | 50 | 0 |

Figure 16:
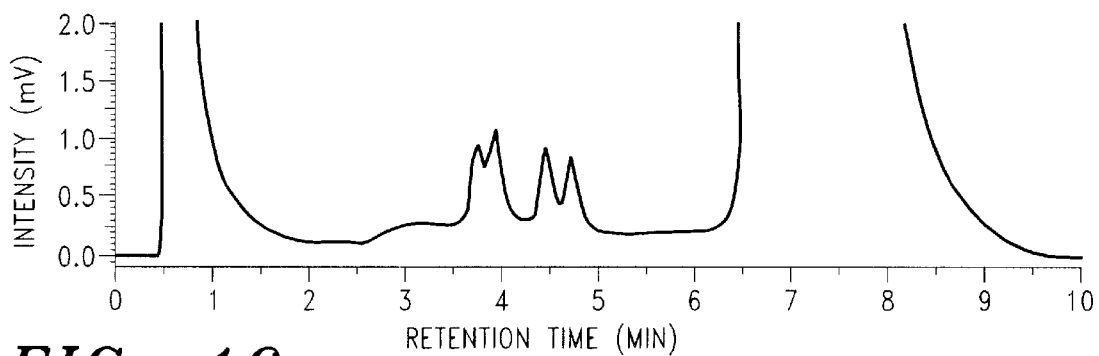
FIG. 16 is a mutation separation profile of a 209 bp homoduplex/heteroduplex mixture using a 50 mm×4.6 mm ID MIPC column prior to injection of Pfu buffer.
Figure 17:
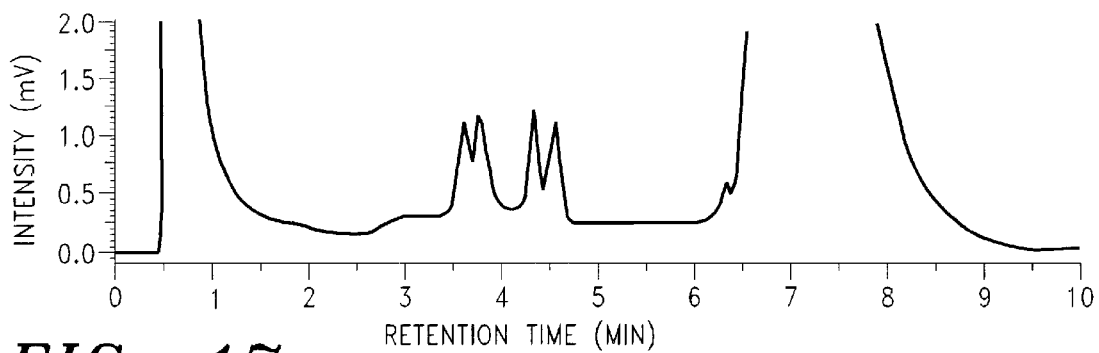
FIG. 17 is a mutation separation profile of a 209 bp homoduplex/heteroduplex mixture using column used in FIG. 16 after repeated injections of Pfu buffer.
Figure 18:
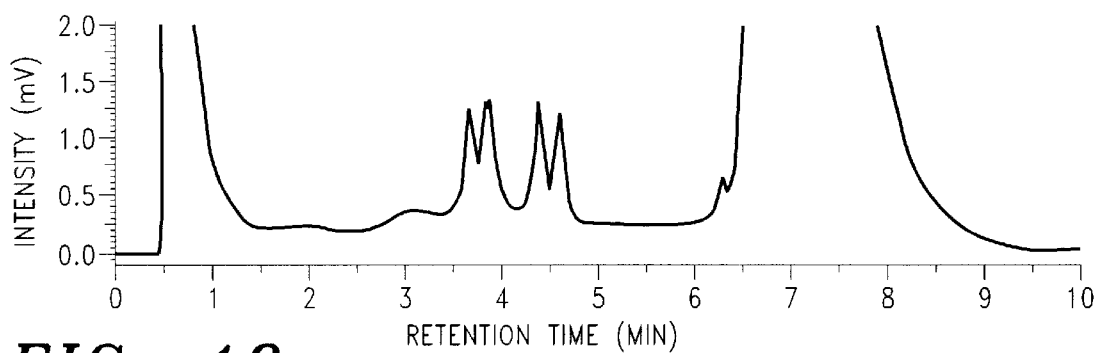
FIG. 18 is a mutation separation profile of a 209 bp homoduplex/heteroduplex mixture using the column used in FIG. 17 after additional injections of Pfu buffer.
Figure 19:
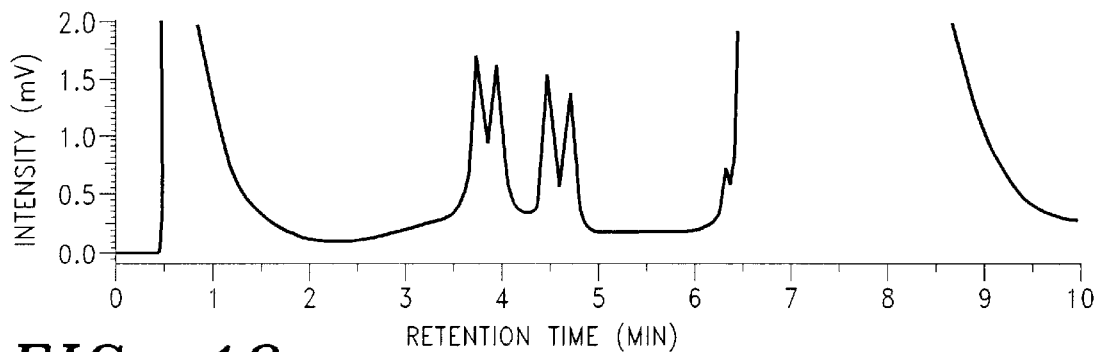
FIG. 19 is a mutation separation profile of a 209 bp homoduplex/heteroduplex mixture using the column used in FIG. 18 after further injections of Pfu buffer.

FIG. 16 shows the separation of the hybridized 209 mutation standard before any injection of Pfu buffer onto the column. FIG. 17 through FIG. 19 show the separation of the 209 standard after every twenty injections of Pfu buffer, for three sets of twenty injections, respectively. All FIGS. 16 through 19 show the heteroduplexes consistently eluting at 3.5 to 4 minutes and the homoduplexes eluting at 4.5 to 5 minutes, with comparable resolution and separation.

EXAMPLE 5

Influence of TWEEN-20 Detergent on Column Performance and Column Lifetime Detergents such as TWEEN-20, TRITON-X100, and NP-40 are present in PCR reagents to solubilize enzymes and keep them in solution. (TWEEN is a registered trademark of ICI Americas Inc. TRITON is a registered trademark of the Rohm and Haas Company.) However, due the hydrophobic and surface active properties of these detergents they might interfere with the separation mechanism on the column and decrease the usable lifetime of the column.

For this Example, a 50 mm×4.6 mm ID DNASep® column (Transgenomic, Inc.) with screw-on PEEK endings was used. The column performance was tested after a series of detergent treatments by analyzing the standard pUC18HaeIII.

Figure 20:
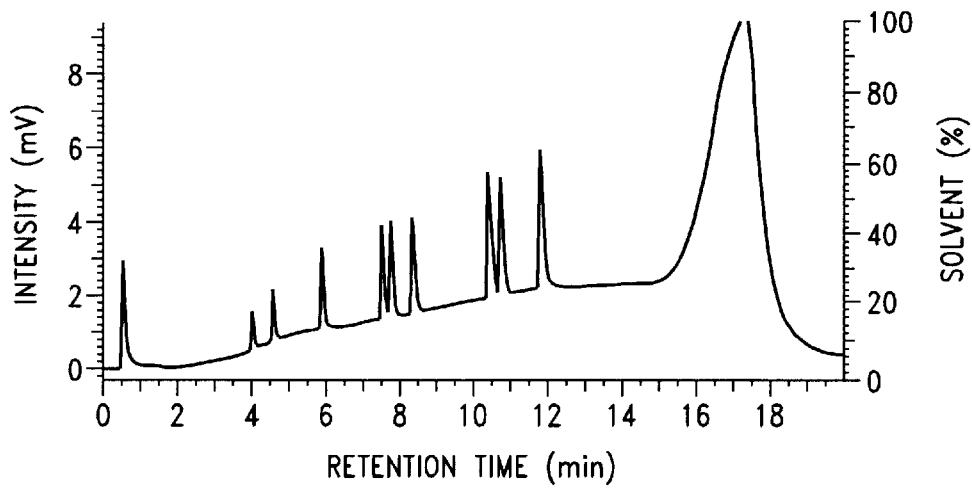
FIG. 20 is a separation profile of a standard mixture of DNA fragments using a 50 mm×4.6 mm ID MIPC column prior to injection of a detergent solution.

FIG. 20 illustrates a pUC18HaeIII digest separation before the column was exposed to detergent. The sample was injected and the column was eluted under the conditions described in Example 1.

Figure 21:
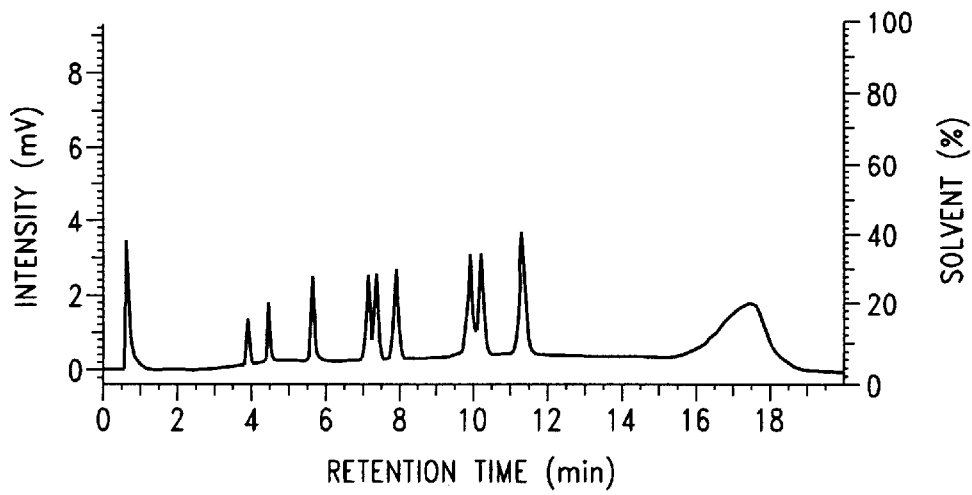
FIG. 21 is a separation profile of a standard mixture of DNA fragments using the column used in FIG. 20 after repeated injections of a detergent solution.

FIG. 21 shows the column after twenty, 15 µL injections of 0.1% (v/v) of aqueous TWEEN-20 (Sigma Chemicals, P-7949) solution. Retention times and resolution decreased and peak fronting was observed.

Figure 22:
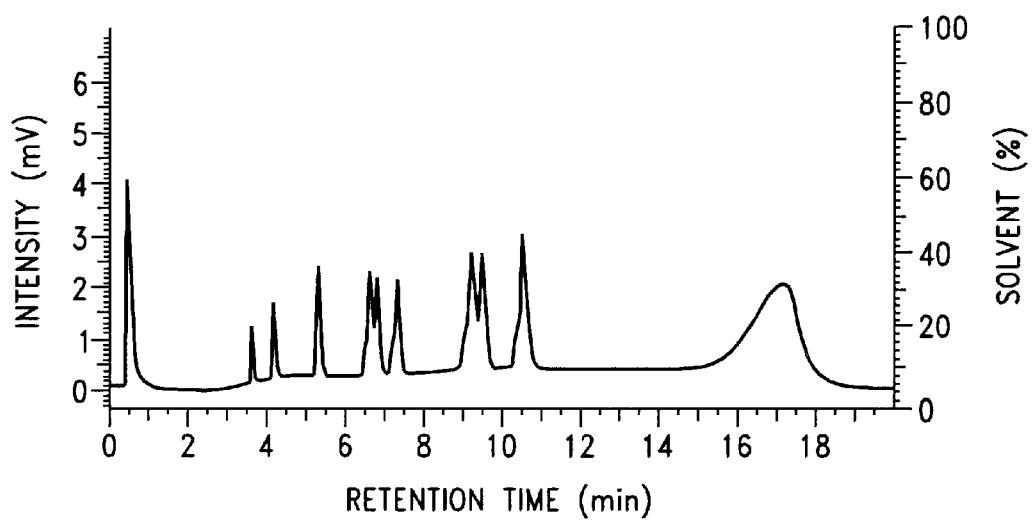
FIG. 22 is a separation profile of a standard mixture of DNA fragments using the column used in FIG. 21 after additional injections of a detergent solution.
Figure 23:
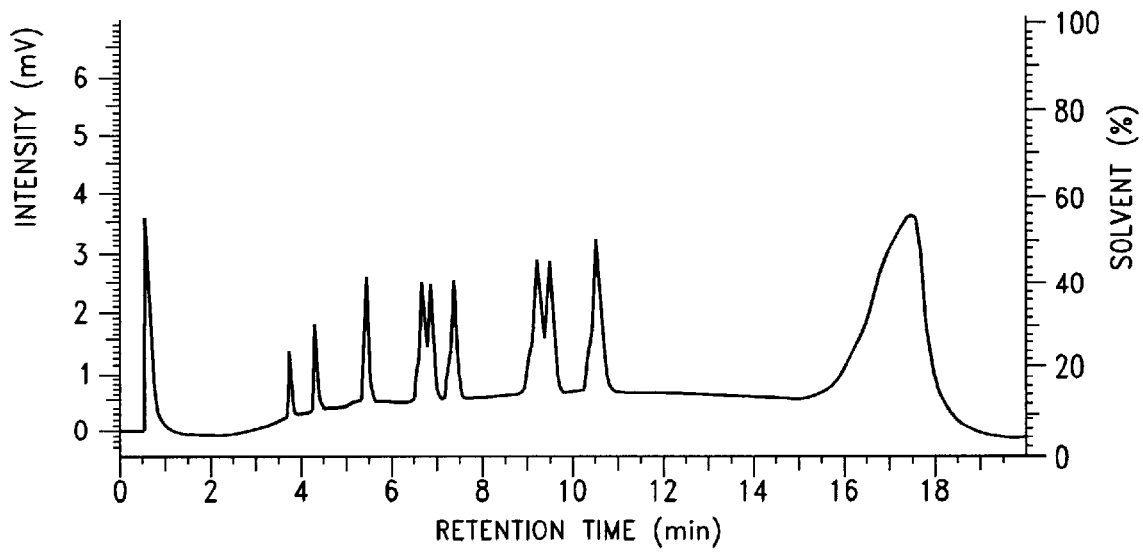
FIG. 23 is a separation profile of a standard mixture of DNA fragments using the column used in FIG. 22 after a treatment with a mobile phase containing acetonitrile.

FIG. 22 shows the same column after another twenty 15 µL injections of 0.1% TWEEN-20. At this point a total of 600 µL of 0.1% TWEEN-20 had been injected onto the column resulting in further deterioration of separation performance FIG. 23 shows the result of an injection of pUC18HaeIIil digest after mobile phase comprising 35%B had been pumped through the column for about 5 hrs at 50° C. and at a rate of 0.75 mL/min. The peaks show fronting, the resolution was deteriorated, and the retention times decreased.

Figure 24:
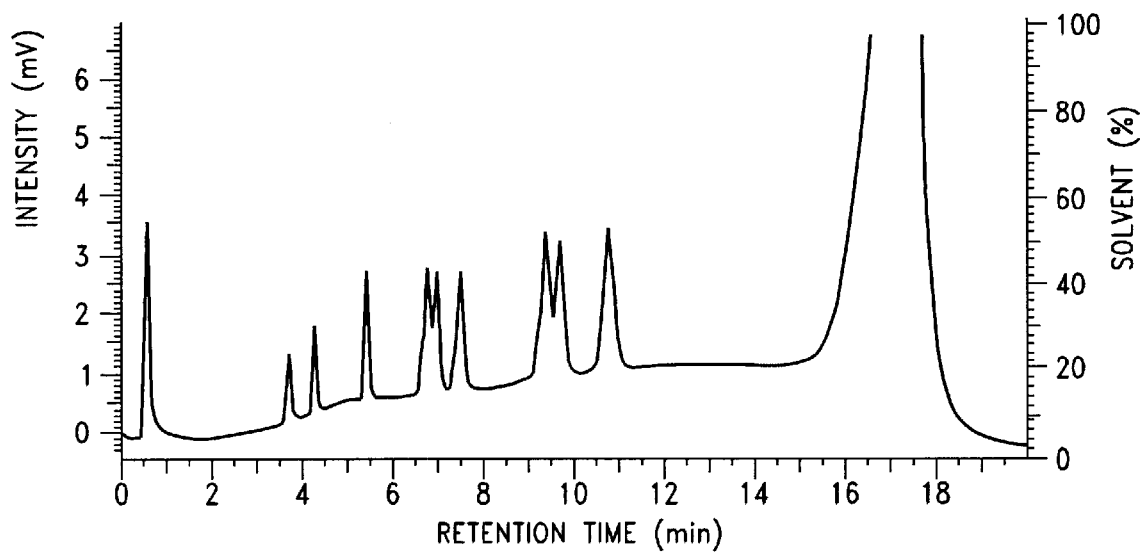
FIG. 24 is a separation profile of a standard mixture of DNA fragments using the column used in FIG. 23 but eluting the fragments with a mobile phase running against the packing direction.

FIG. 24 shows the result of an injection of pUC18HaeIII digest onto the column described in FIG. 23 but running mobile phase against the packing direction. This was done to show whether the fronting was due to a ruptured column bed. Fronting was still visible, indicating that the column bed was not ruptured.

Figure 25:
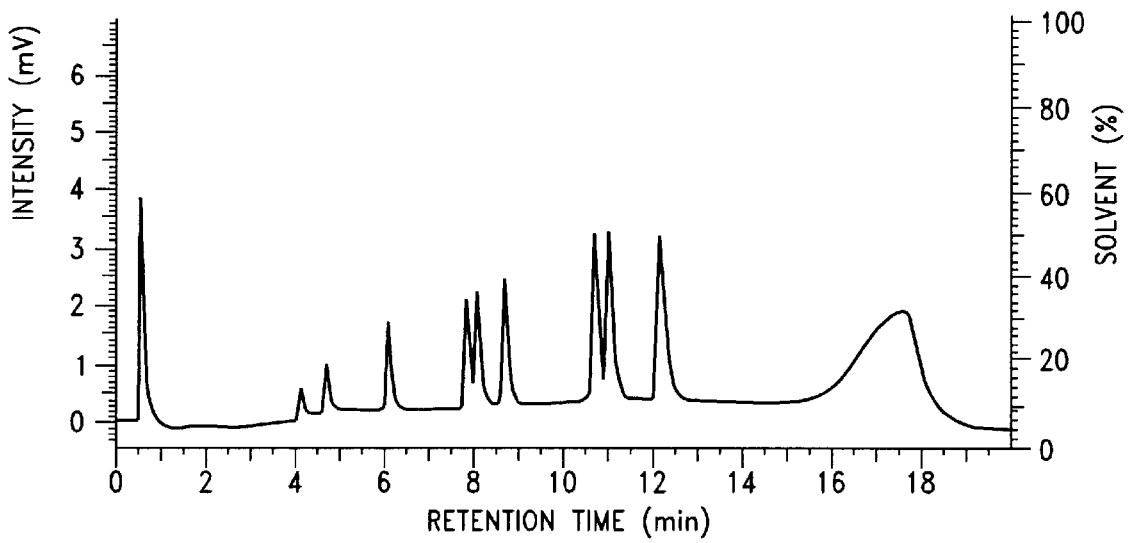
FIG. 25 is a separation profile of a standard mixture of DNA fragments using the column used in FIG. 23 after a methanol wash treatment.

FIG. 25 shows the result of an injection of pUC18HaeIII digest onto the column used in FIG. 24 after a 45 minute washing step (at a column temperature of 50° C.) with 100% methanol.

Figure 26:
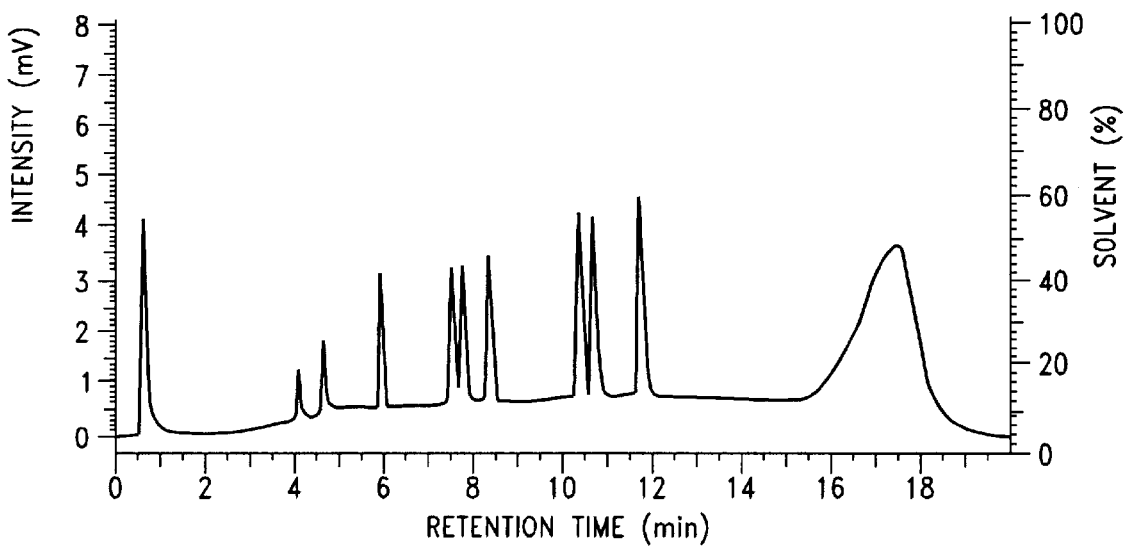
FIG. 26 is a separation profile of a standard mixture of DNA fragments using the column used in FIG. 25 after repeated injections of the standard mixture.

FIG. 26 shows the result of an injection of pUC18HaeIII digest onto the column used in FIG. 25 after 3 days during which about thirty pUC18HaeIII digest separations were performed. No deterioration in the separation performance was visible.

Figure 27:
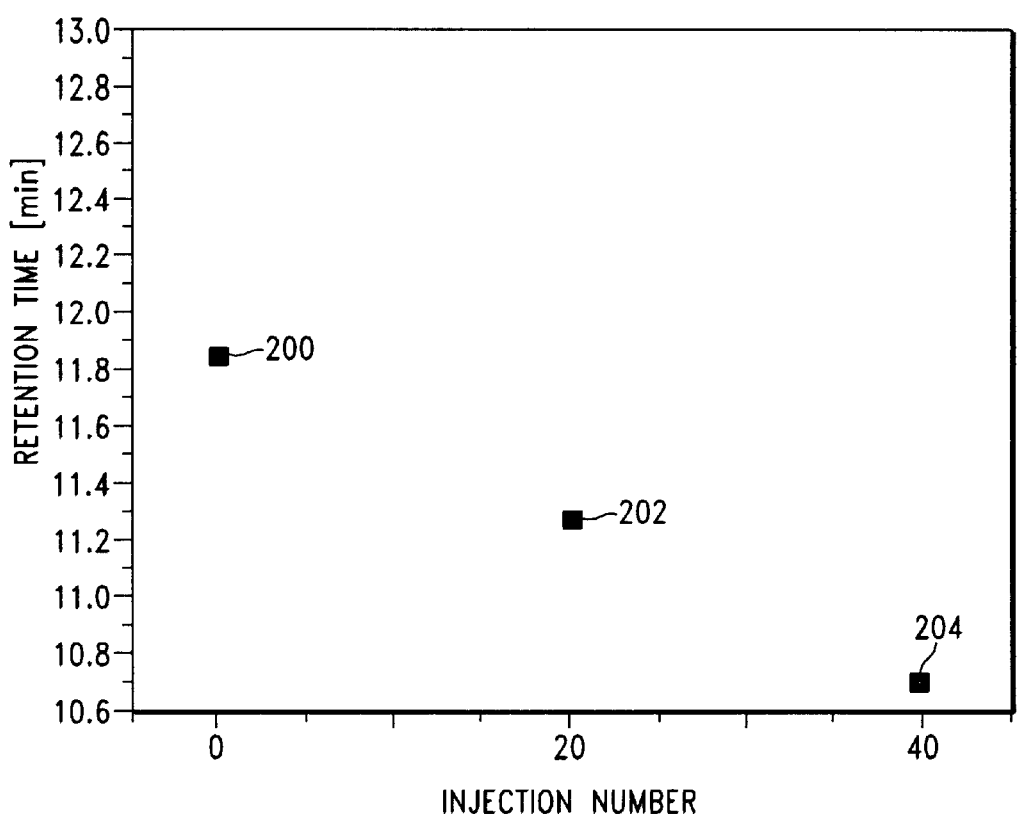
FIG. 27 illustrates the effect of detergent injections on the MIPC retention time of a standard DNA fragment.

FIG. 27 summarizes results from FIGS. 20–22. Data point 200 indicates the retention time (Rt) of the 587 bp peak prior to the TWEEN-20 injections. Data point 202 indicates the Rt of the 587 bp peak after twenty, 15 µL injections of 0.1% TWEEN-20 solution. Data point 204 indicates the Rt of the 587 bp peak after twenty more injections of 0.1% TWEEN-20 solution.

EXAMPLE 6

Treatment of Separation Column with EDTA Solution

After every 200 injections, the column is treated by two injections 100 µL of 0.2M aqueous EDTA solution and eluting the column after each injection using the elution conditions as described in Example 1.

EXAMPLE 7

While the foregoing has presented specific embodiments of the present invention, it is to be understood that these embodiments have been presented by way of example only. It is expected that others will perceive and practice variations which, though differing from the foregoing, do not depart from the spirit and scope of the invention as described and claimed herein.

The invention claimed is:

1. A process for cleaning the non-polar polynucleotide separation surfaces in an apparatus for effecting separations of polynucleotide fragments by reverse phase ion pairing chromatography, the apparatus comprising a separation column containing separation media having non-polar polynucleotide separation surfaces, separation solution supply means, a separation solution conduit communicating with the separation column and the separation solution supply means, and a cleaning solution valve means positioned in the separation solution conduit for injecting cleaning solution into the separation solution conduit, the process comprising interrupting the flow of separation solvent with a block of cleaning solution injected into the flow of separation solution passing to the column, the cleaning solution containing agent which removes accumulated residues from the non-polar surface.

2. The process of claim 1 herein said polynucleotides comprise DNA.

3. The process of claim 1 wherein said polynucleotides comprise RNA.

4. The process of claim 1 wherein said polynucleotides comprise double-stranded pglynucleotides.

5. The process of claim 1 wherein said polynucleotides comprise single-stranded polynucleotides.

6. The process of claim 1 wherein the cleaning solution comprises an enzyme which will cleave DNA.

7. The process of claim 4 wherein the cleaning solution pH is from 8 to 13.

8. The process of claim 1 wherein the cleaning solution comprises a chelating agent.

9. The process of claim 8 wherein said chelating agent comprises EDTA.

10. The process of claim 1 wherein the cleaning solution comprises an organic solvent, the solution having a concentration of organic solvent of at least about 50% by volume of said organic solvent.

11. The process of claim 10 wherein said organic solvent is methanol or acetonitrile.

12. The process of claim 10 wherein said cleaning solution comprises 100% methanol.

13. The process of claim 10 wherein said cleaning solution comprises at least about 70% acetonitrile.

14. The process of claim 1 wherein said cleaning solution comprises aqueous nitric acid.

15. The process of claim 1 wherein the cleaning solution comprises an enzyme which will cleave RNA.

\* \* \* \* \*